United States Patent
Tsukida et al.

(10) Patent No.: US 7,223,779 B2
(45) Date of Patent: May 29, 2007

(54) AZASUGAR DERIVATIVE AND DRUG CONTAINING THE SAME AS THE ACTIVE INGREDIENT

(75) Inventors: Takahiro Tsukida, Osaka (JP); Hideki Moriyama, Sapporo (JP); Koichi Yokota, Sakai (JP); Mariko Hatakeyama, Osaka (JP); Shinichiro Nishimura, Sapporo (JP)

(73) Assignee: Carna Biosciences Inc., Kobe-shi (JP)

( * ) Notice: Subject to any disclaimer, the term of this patent is extended or adjusted under 35 U.S.C. 154(b) by 269 days.

(21) Appl. No.: 10/504,777

(22) PCT Filed: Jun. 26, 2003

(86) PCT No.: PCT/JP03/08112

§ 371 (c)(1),
(2), (4) Date: Mar. 14, 2005

(87) PCT Pub. No.: WO2004/002959

PCT Pub. Date: Jan. 8, 2004

(65) Prior Publication Data
US 2005/0154017 A1   Jul. 14, 2005

(30) Foreign Application Priority Data
Jun. 26, 2002   (JP) ............... 2002-186479

(51) Int. Cl.
*A61K 31/44* (2006.01)
*C07D 211/40* (2006.01)

(52) U.S. Cl. .................. 514/354; 546/220
(58) Field of Classification Search ............ 514/354; 546/220
See application file for complete search history.

(56) References Cited

FOREIGN PATENT DOCUMENTS

WO   WO 2004/060875   7/2004

OTHER PUBLICATIONS

Koulocheri et. al., "Asymmetric synthesis of (2R, 3S)-h-hydroxypipecolic acid sigma—lactam derivatives", Tetrahdron 58 (2002), pp. 6665-6671.*
Uli Kazmaier et al.; European Journal of Organic Chemistry, Chemical abstracts, vol. 129, No. 9, pp. 1833-1840, 1998. Cited in the enclosed international search report.
Chinese Office Action dated Apr. 28, 2006, issued in corresponding Chinese patent application No. 038150190.
Supplementary European Search Report dated Jun. 22, 2006, issued in corresponding European patent application No. 03736257.1.
Roland Grandel et al., A Short Synthesis of Azasugars via Aldol Reaction of Chelated Amino Acid Ester Enolates, Tetrahedron Letters, vol. 38, 1997, pp. 8009-8012, No. 46, Elsevier Science Ltd., Great Britain.

* cited by examiner

*Primary Examiner*—Thomas McKenzie
*Assistant Examiner*—Binta Robinson
(74) *Attorney, Agent, or Firm*—Westerman, Hattori, Daniels & Adrian, LLP.

(57) ABSTRACT

A novel azasugar derivative, and a drug containing the same as an active ingredient are disclosed. The drug is useful for treatment of keratinocyte-proliferative diseases.

3 Claims, 1 Drawing Sheet

AZASUGAR DERIVATIVE AND DRUG CONTAINING THE SAME AS THE ACTIVE INGREDIENT

TECHNICAL FIELD

The present invention relates to a novel hydroxamic acid compound having an azasugar structure and, more particularly, to an azasugar derivative represented by the following general formula (A):

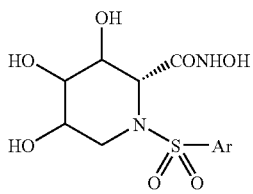

(A)

wherein Ar represents a phenyl group which may have a substituent at the p-position, or the following general formula (I):

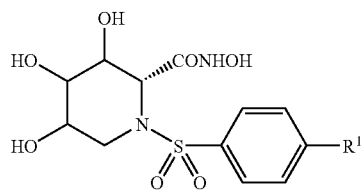

(I)

wherein $R^1$ represents a hydrogen atom, a halogen atom, a hydroxyl group, an amino group, a $C_1$–$C_8$ alkyl group, a phenyl group, a phenoxy group, a $C_1$–$C_8$ alkoxy group (said $C_1$–$C_8$ alkoxy group may be substituted with a $C_1$–$C_4$ alkoxy group or a $C_1$–$C_4$ alkylthio group) or a heteroallyloxy group, or a pharmaceutically acceptable salt thereof, and a drug containing the same as an active ingredient.

Also the present invention is related to a compound which is useful as an intermediate for preparation of the above compound (A) and is represented by the following formula (IIA) or (IIB):

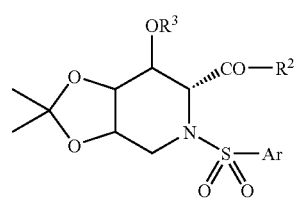

(IIA)

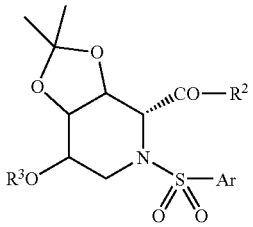

(IIB)

wherein Ar represents a phenyl group which may have a substituent at the p-position, CO—$R^2$ represents a hydroxamic acid equivalent, and $OR^3$ represents a hydroxyl group equivalent.

BACKGROUND ART

Taking notice of high coordinative ability to metal atoms, various hydroxamic acid compounds have been developed as a metalloenzyme inhibitor. Although peptide-based compounds have mostly been developed (see, for example, WO94/02447 and WO90/05719), various compounds containing sulfonic acid amide in a partial structure have recently been published and, for example, European Patent Publication (EP1081137) discloses a compound having the same N-sulfonylpiperidine-2-hydroxamic acid structure as that of the compound of the present invention as an aggrecan degrading enzyme inhibitor.

For a metalloenzyme as a target of inhibition, for example, MMP (WO90/05716) such as collagenases, stromelysins and gelatinases, TNF-α producing enzyme (WO 94/10990) and Fas ligand solubilization enzyme (WO 97/09066) have become of major interest in view of the development of medicaments.

It is known that EGF family growth factors are synthesized as membrane-bound proteins as precursors which are broken into a soluble form by action of the metalloenzyme, and thus the resulting soluble ligand binds to EGF receptors. In case of HB-EGF among them, the solubilization process plays an important role in the proliferation of keratinocytes (WO 01/70269). Said publication discloses that a hydroxamic acid derivative having a tetrahydroisoquinoline skeleton inhibits a solubilizing enzyme of HB-EGF and is useful as a remedy for keratinocyte-proliferative diseases.

DISCLOSURE OF THE INVENTION

An object of the present invention is to provide a novel remedy for keratinocyte-proliferative diseases.

The present inventors have intensively studied and found that a hydroxamic acid compound having an azasugar structure represented by the above general formula (A) inhibits solubilization of HB-EGF and is useful as a remedy for keratinocyte-proliferative diseases, and thus the present invention has been completed.

The present invention will now be described in detail.

BEST MODE FOR CARRYING OUT THE INVENTION

Figure 1:
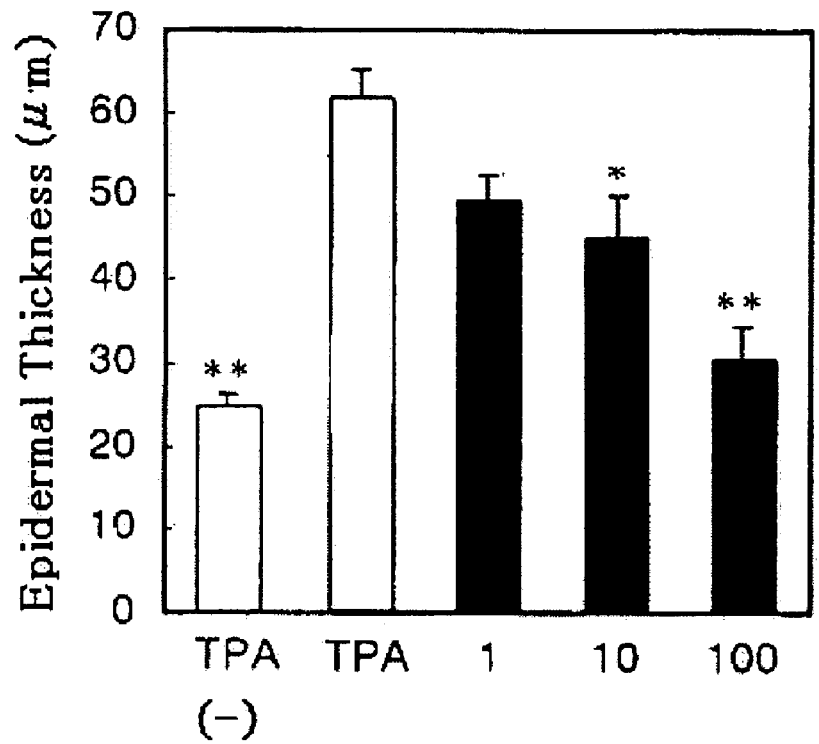
FIG. 1 is a graph showing hyperplasia inhibitory activity by virtue of a compound of Example 4.

The present invention is directed to a compound represented by the general formula (A):

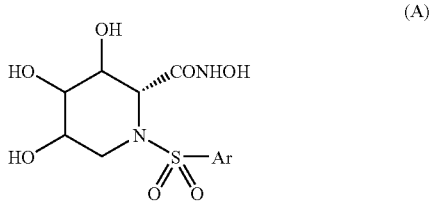

(A)

wherein Ar represents a phenyl group which may have a substituent at the p-position, or a pharmaceutically acceptable salt thereof. The substituent as used herein includes, for example, a halogen atom, a hydroxyl group, an amino group, a $C^1$–$C_8$ alkyl group, a phenyl group, a phenoxy group, a $C_1$–$C_8$ alkoxy group (said $C_1$–$C_8$ alkoxy group may be substituted with a $C_1$–$C_4$ alkoxy group or a $C_1$–$C_4$ alkylthio group), or a heteroallyloxy group. Among these substituents, a methoxy group, a 2-ethoxyethoxy group or a phenoxy group is particularly preferable.

The compound (A) of the present invention can be prepared from a compound (IIA) or (IIB):

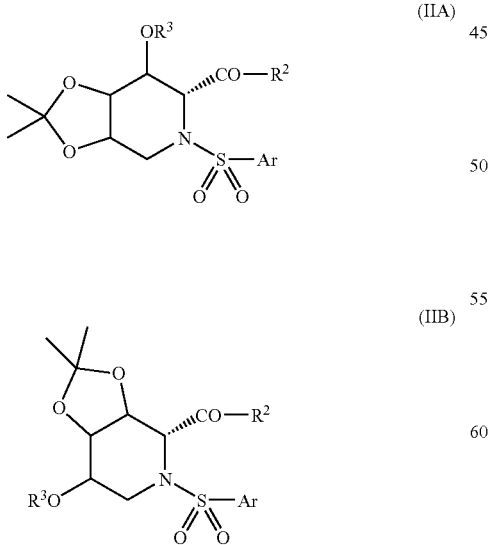

wherein Ar represents a phenyl group which may have a substituent at the p-position, CO—$R^2$ represents a hydroxamic acid equivalent, and $OR^3$ represents a hydroxyl group equivalent, by the method described hereinafter.

Similar to the above, the substituent includes, for example, a halogen atom, a hydroxyl group, an amino group, a $C_1$–$C_8$ alkyl group, a phenyl group, a phenoxy group, a $C_1$–$C_8$ alkoxy group (said $C_1$–$C_8$ alkoxy group may be substituted with a $C_1$–$C_4$ alkoxy group or a $C_1$–$C_4$ alkylthio group) or a heteroallyloxy group.

Furthermore, the hydroxamic acid equivalent as used herein means a monovalent atomic group CONHOH itself and a functional group which can be chemically converted into said atomic group CONHOH by a conventional method, and $R^2$ includes, for example, a methoxy group, an ethoxy group, or a benzyloxyamino group. Since said benzyloxyamino group can be easily introduced by the condensation reaction between carboxylic acid and benzyloxyamine, the hydroxamic acid equivalent includes a carboxyl group and various esters which can be easily converted into a carboxyl group. Therefore carboxylic acid protected with various carboxylprotective groups is included and $R^2$ includes, for example, a benzyloxy group and a tert-butyloxy group, in addition to the methoxy group, the ethoxy group and the benzyloxyamino group.

The hydroxyl group equivalent as used herein means a hydroxyl group itself and a functional group which can be chemically converted into a hydroxyl group by a conventional method, and $R^3$ means a hydrogen atom, and alcohol protective group such as acetyl group, benzyl group, tert-butyl group, and tetrahydropyranyl group.

Among the compound (IIA) or (IIB), a compound represented by the following formula (IIIA) or (IIIB):

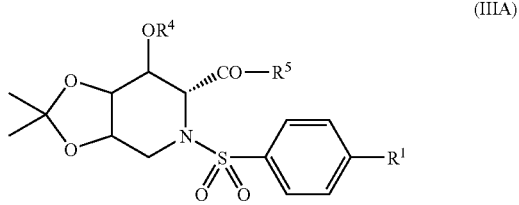

(IIIA)

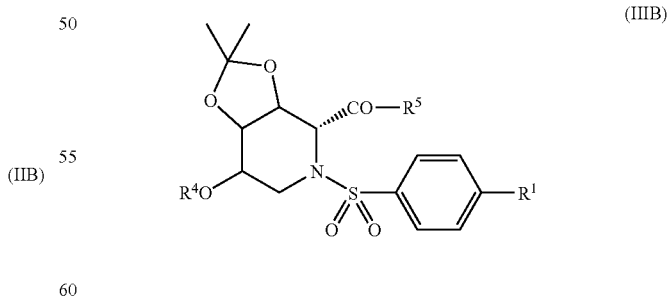

(IIIB)

wherein $R^1$ represents a hydrogen atom, a halogen atom, a hydroxyl group, an amino group, a $C_1$–$C_8$ alkyl group, a phenyl group, a phenoxy group, a $C_1$–$C_8$ alkoxy group (said $C_1$–$C_8$ alkoxy group may be substituted with a $C_1$–$C_4$ alkoxy group or a $C_1$–$C_4$ alkylthio group) or a heteroallyloxy group, $R^4$ represents a hydrogen atom or an acetyl group, and $R^5$ represents a benzyloxyamino group, a benzyloxy group, a methoxy group or an ethoxy group, is particularly preferably used.

The compound of the general formula (A) includes all stereoisomers represented by the following formula:

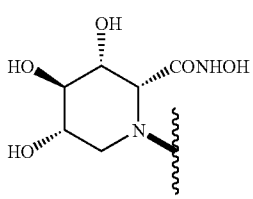
(Ia)

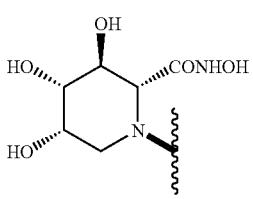
(Ib)

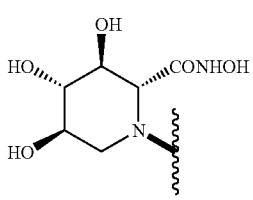
(Ic)

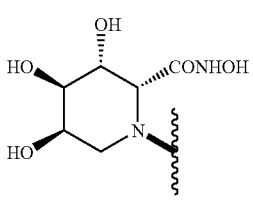
(Id)

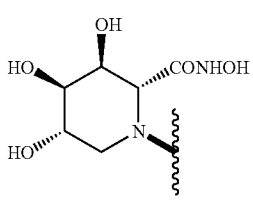
(Ie)

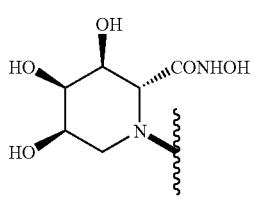
(If)

-continued

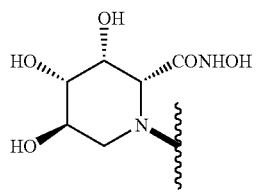
(Ig)

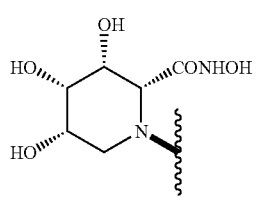
(Ih)

or a mixture thereof, and the compound (Id) is particularly preferable.

Similarly, the compound (IIA) or (IIB) and the compound (IIIA) or (IIIB) respectively include corresponding eight kinds of stereoisomers or a mixture thereof. Abbreviations and symbols used in the following descriptions mean as follows.

Ac: Acetyl group
AcOCs: Cesium acetate
Bn: Benzyl group
DEAD: Diethyl azodicarboxylate
DIEA: Diisopropylethylamine
DMF: N,N-dimethylformamide
DMP: 2,2-Dimethoxypropane
DMAP: 4-Dimethylaminopyridine
DCC: Dicyclohexylcarbodiimide
WSC: 1-Ethyl-3-(dimethylaminopropyl)carbodiimide hydrochloride
HOBt: 1-Hydroxy-1H-benzotriazole
HPLC: High-performance liquid chromatography
THF: Tetrahydrofuran
TBAF: 1.0M THF solution of tetrabutylammonium fluoride
Pd—C: Palladium-carbon
Pd(OH)$_2$/C: Palladium hydroxide-carbon
PPh$_3$: Triphenylphosphine
NaOMe: Sodium methylate
NH$_2$OBn: Benzylhydroxylamine hydrochloride
18-Crown-6: 18-Crown-6
MsCl: Mesyl chloride
Tf$_2$O: Trifluoromethanesulfonic anhydride The compound (A) of the present invention can be prepared by the method described below.

1. Preparation of Stereoisomers (Ie) and (Ig) of Compound (I):

For example as shown in the following scheme (Scheme 1):

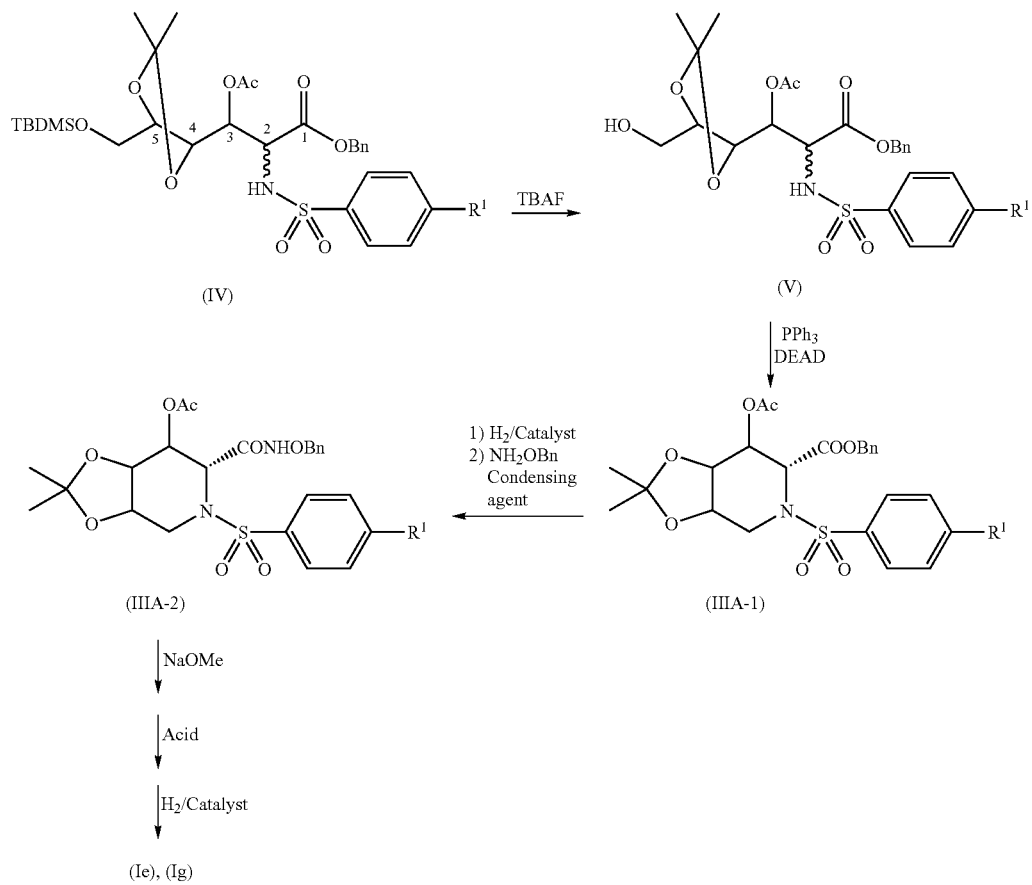

(wherein TBDMS represents a tert-butyldimethylsilyl group and $R^1$ is as defined above), stereoisomers (Ie) and (Ig) can be prepared by deprotecting a compound (IV) obtained by reacting D- or L-threitol with a glycine derivative [see Tetrahedron Letters, Vol. 38, No. 46, 8009–8012 (1997)] and performing the ring closure reaction to obtain a precursor (IIIA-1), followed by deprotection and chemical conversion of a functional group.

First, a protective group (TBDMS) of a primary hydroxyl group of the compound (IV) [see Tetrahedron Letters, Vol. 38, No. 46, 8009–8012 (1997)] is deprotected to obtain a compound (V). The reaction is usually conducted by adding TBAF in an inert solvent such as THF and stirring at 0° C. to room temperature for 30 minutes to 2 hours.

Then, the compound (V) is cyclized by the Mitsunobu reaction to obtain a compound (IIIA-1). The reaction can be conducted for example by adding triphenylphosphine and DEAD in an inert solvent such as THF and stirring at 0° C. to room temperature for 30 minutes to 4 hours. In this case, since a mixture derived from epimerization of asymmetric carbon at the α-position of the benzyloxycarbonyl group of the compound (IIIA-1) may appear, the compound (IIIA-1) is subjected to the following reaction after separation and purification by various chromatography means such as HPLC. Alternatively, the compound (IIIA-1) may be subjected to the following reaction in the form of a mixture and may be separated and purified in any stage.

The resulting precursor (IIIA-1) can be converted into the objective stereoisomers (Ie) or (Ig) by converting a benzyloxycarbonyl group into a benzyloxyaminocarbonyl group and performing deprotection of each group.

First, a benzyl ester moiety of the compound (IIIA-1) is cleaved and removed by hydrogenolysis, followed by condensation with benzylhydroxylamine to obtain a compound (IIIA-2). The hydrogenolysis is usually conducted by optionally adding water in ethyl acetate, lower alcohol such as methanol, or 1,4-dioxane, and stirring in the presence of a catalyst such as 10% palladium-carbon, 20% palladium hydroxide-carbon or platinum under a hydrogen gas flow or pressure at room temperature to 60° C. for 1 to 5 hours. The following condensation is usually conducted by using a condensing agent such as DCC or WSC and stirring at 0° C. to room temperature for 2 to 24 hours in the presence of an optional auxiliary condensing agent such as HOBt. The molar ratios of the reactants are 0.8 to 1.5 mols of benzylhydroxylamine, 1.0 to 1.5 mol of the condensing agent and 1.0 to 1.5 mol of the auxiliary condensing agent based on 1 mol of the carboxylic acid compound.

Then, each protective group of the compound (IIIA-2) is cleaved and removed to obtain the objective compound. The acetyl group, the acetonide group and the benzyl group may be cleaved and removed by a conventional method. For example, the deacetylation reaction is usually conducted by adding 28% NaOMe in a lower alcohol such as methanol and stirring at 0° C. to room temperature for 1 to 6 hours. For example, the acetonide group is cleaved and removed by optionally adding water in a solvent such as methanol in the presence of a cation exchange resin and reacting at room temperature to 50° C. for 2 to 24 hours. The benzyl group can be cleaved and removed by hydrogenolysis in the same manner as described above.

In Scheme 1, a compound (IVe) as a (3S,4S,5R) isomer of the compound (IV) may be used so as to obtain the stereoisomer (Ie) and a compound (IVg) as a (3R,4R,5S) isomer of the compound (IV) may be used so as to obtain the stereoisomer (Ig) (the numbering is based on hexanoic acid). The compound (IVe) or (IVg) can be derived from the reaction between a glycine derivative and L-threitol or D-threitol respectively.

2. Preparation of Stereoisomers (If) and (Ih) of Compound (I):

For example as shown in the following scheme (Scheme 2):

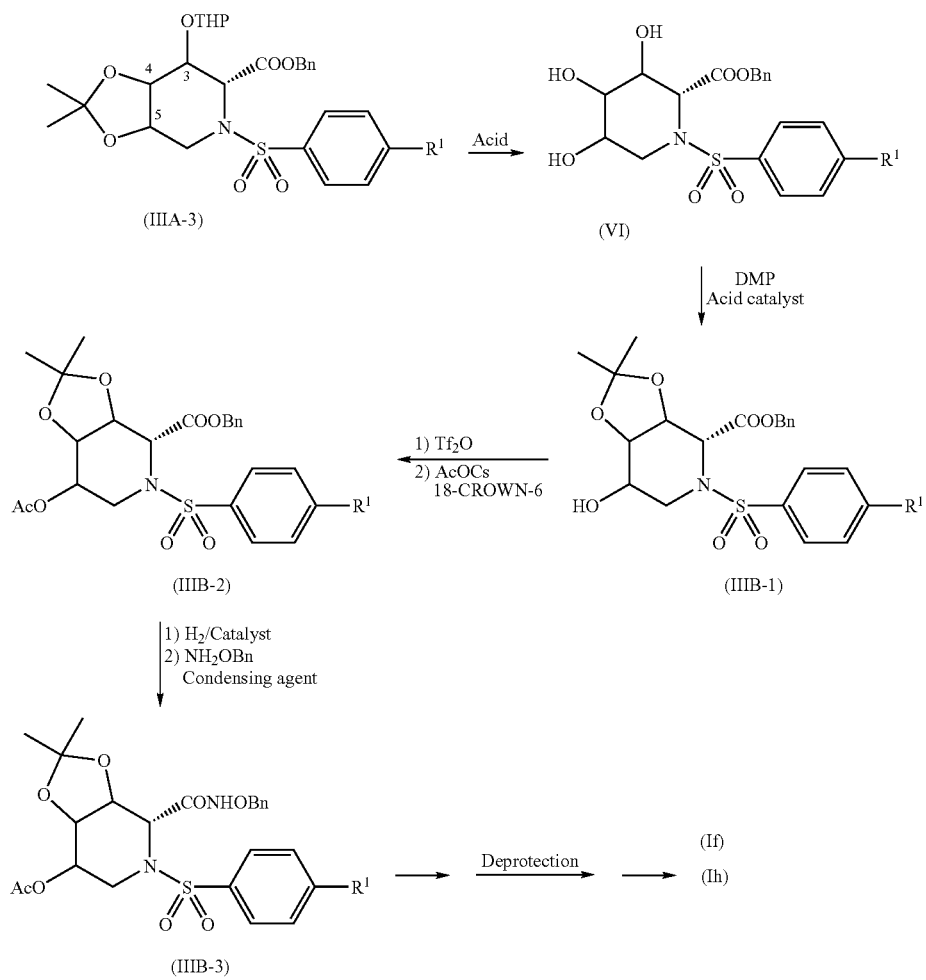

(wherein THP represents a tetrahydropyranyl group and $R^1$ is as defined above), stereoisomers (If) and (Ih) can be prepared by protecting hydroxyl groups at the 3- and 4-positions of the stereoisomer (Ie) or (Ig) with an acetonide group and performing steric inversion of a hydroxyl group at the 5-position (the numbering is based on the piperidine ring).

First, protective groups (tetrahydropyranyl group and acetonide group) of a compound (IIIA-3), which can be synthesized in the same manner as in case of the compound (IIIA-1) shown in Scheme 1, are cleaved and removed to obtain a compound (VI). In the reaction, according to the method using the cation exchange resin used in the cleavage of the above acetonide group, both protective groups can be simultaneously cleaved and removed.

Then, acetonidation of the compound (VI) is conducted to obtain a compound (IIIB-1). The reaction can be conducted by adding a 5- to 15-fold amount of DMP in an inert solvent such as DMF in the presence of an acid catalyst such as p-toluenesulfonic acid monohydrate or camphor-10-sulfonic acid and reacting at room temperature to 80° C. for 2 to 24 hours.

A hydroxyl group of the compound (IIIB-1) is converted into a triflate group and then steric inversion is caused by the $S_N2$ nucleophilic substitution reaction to obtain a compound (IIIB-2). The reaction for preparation of a triflate compound is usually conducted by adding trifluoromethanesulfonic anhydride in a solvent such as methylene chloride in the presence of a base such as triethylamine or pyridine at −60 to 0° C. and stirring at the same temperature for 30 minutes to 2 hours. In this case, the resulting triflate compound is subjected to the following reaction immediately after the completion of the reaction without being purified, or can be subjected to the following reaction immediately after purification by silica gel column chromatography. The following $S_N2$ nucleophilic substitution reaction can be conducted by adding cesium acetate in a solvent such as acetonitrile in the presence of 18-Crown-6 and stirring at 0° C. to room temperature for 1 to 24 hours.

A benzyl ester moiety of the compound (IIIB-2) is cleaved and removed by hydrogenolysis, followed by condensation with benzylhydroxylamine to obtain a compound (IIIB-3). Subsequently, the respective protective groups, for example, an acetyl group, an acetonide group and a benzyl group of the compound (IIIB-3) are cleaved and removed in any order to obtain the objective stereoisomer (If) or (Ih). The reaction conditions are the same as in Scheme 1.

3. Preparation of Stereoisomers (Ia), (Ib), (Ic) and (Id) of Compound (I):

Stereoisomers (Ia), (Ib), (Ic) and (Id) can be prepared through the following scheme (Scheme 3):

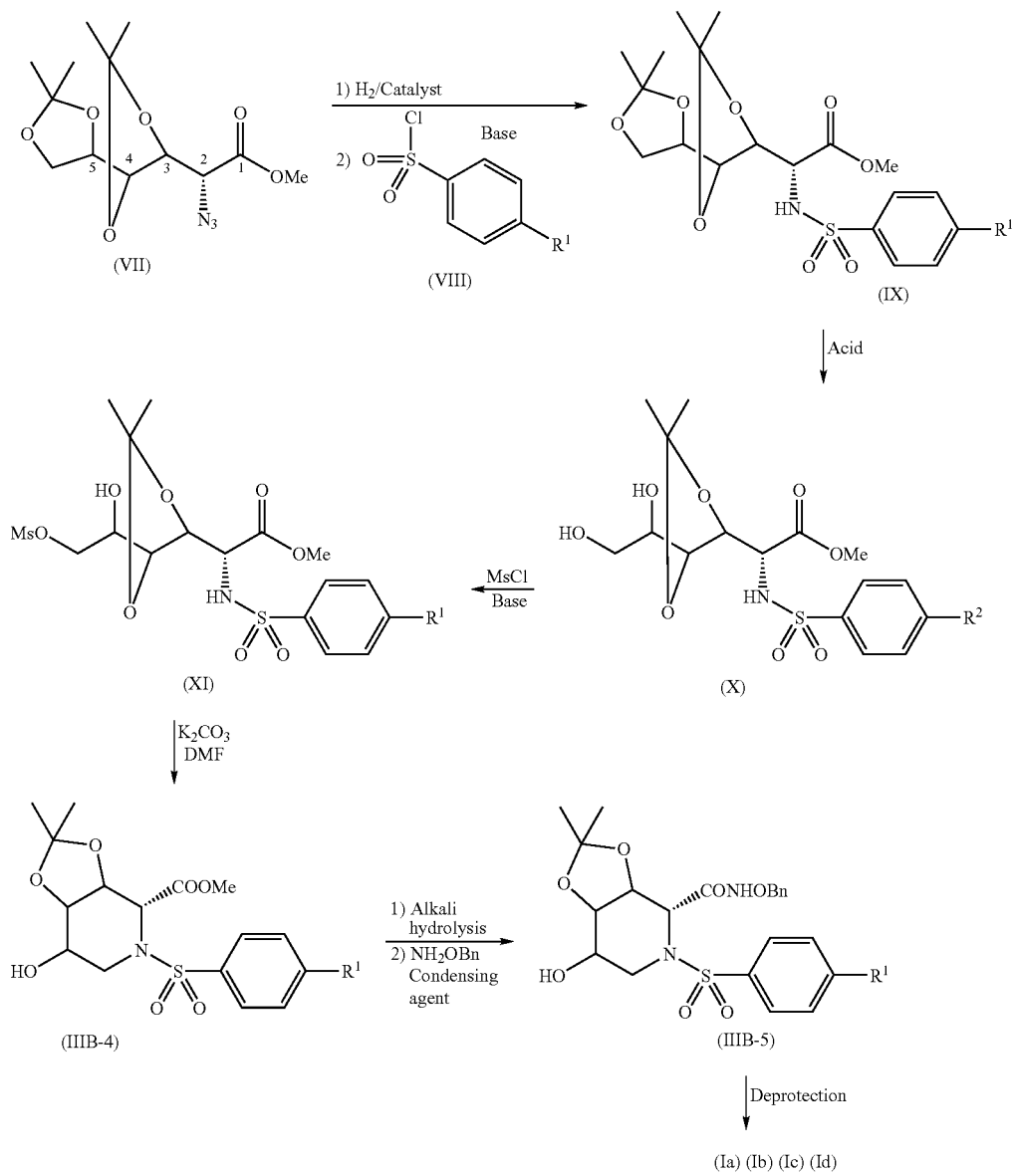

(wherein R¹ is as defined above).

First, an azide group of a compound (VII) [see Synthesis, No. 9, 1305–1309 (2000)] is reduced, followed by reaction with allylsulfonyl chloride (VIII) to obtain a compound (IX). For example the reduction of the azide group can be conducted by optionally adding water in ethyl acetate, lower alcohol or 1,4-dioxane, and stirring in the presence of a catalyst such as 10% palladium-carbon, 20% palladium hydroxide-carbon or platinum under a hydrogen gas flow or pressure at room temperature to 60° C. The following reaction with allylsulfonyl chloride (VIII) is usually conducted in an inert solvent such as DMF in the presence of a base such as DMAP by stirring at 0° C. to room temperature for 1 to 24 hours.

Then, a terminal acetonide group of the compound (IX) is selectively cleaved and removed. The reaction is usually conducted by optionally adding water in a solvent such as methanol in the presence of a cation exchange resin and stirring at room temperature to 50° C. for 5 hours to 4 days. Alternatively, the objective compound (X) can also be obtained by stirring in acetonitrile at room temperature for 0.5 to 2 hours using cerium chloride heptahydrate and oxalic acid.

Then, a primary hydroxyl group of the compound (X) is selectively converted into a mesyl group. The reaction is conducted by stirring in a solvent such as methylene chloride in the presence of a base such as triethylamine or DIEA at low temperature preferably ranging from −60 to −20° C. for 30 minutes to 5 hours using 0.95 to 1.05 mol of mesyl chloride to obtain the objective compound (XI).

Then, a compound (IIIB-4) is obtained by the intramolecular ring closure reaction of the compound (XI). The reaction is usually conducted in an inert solvent such as DMF in the presence of a base such as potassium carbonate or triethylamine at room temperature to 100° C., and preferably 40 to 60° C. for 1 to 5 hours to obtain the objective compound (IIIB-4).

An ester moiety of the compound (IIIB-4) is converted into corresponding carboxylic acid by alkaline hydrolysis, which is then condensed with benzylhydroxylamine without being purified to obtain a compound (IIIB-5). The alkaline hydrolysis is usually conducted by stirring in a lower alcohol such as methanol at 0 to 60° C. for 1 to 5 hours using an aqueous sodium hydroxide or lithium hydroxide solution, and preferably an aqueous 1N solution of the hydroxide. Subsequently, an acetonide group and a benzyl group are cleaved and removed to obtain a compound (Ia), (Ib), (Ic) or (Id). These reactions may be conducted in the same manner as in Scheme 1 or 2.

In Scheme 3, a compound (VIIa) as a (3R,4S,5S) isomer of the compound (VII) may be used so as to obtain the stereoisomer (Ia), a compound (VIIb) as a (3S,4R,5S) isomer of the compound (VII) may be used so as to obtain the stereoisomer (Ib), a compound (VIIc) as a (3S,4R,5R) isomer of the compound (VII) may be used so as to obtain the stereoisomer (Ic), and a compound (VIId) as a (3R,4S, 5R) isomer of the compound (VII) may be used so as to obtain the stereoisomer (Id) (the numbering is based on hexanoic acid). The compound (VIIa) can be prepared from L-gulono-1,4-lactone, the compound (VIIb) can be prepared from L-glucono-1,5-lactone, the compound (VIIc) can be prepared from D-gulono-1,4-lactone, and the compound (VIId) can be prepared from D-manno-1,4-lactone [Synthesis, 9, 1305–1309 (2000)].

4. Another Method for Preparation of Stereoisomer (Id) of Compound (I):

According to the following scheme (Scheme 4)

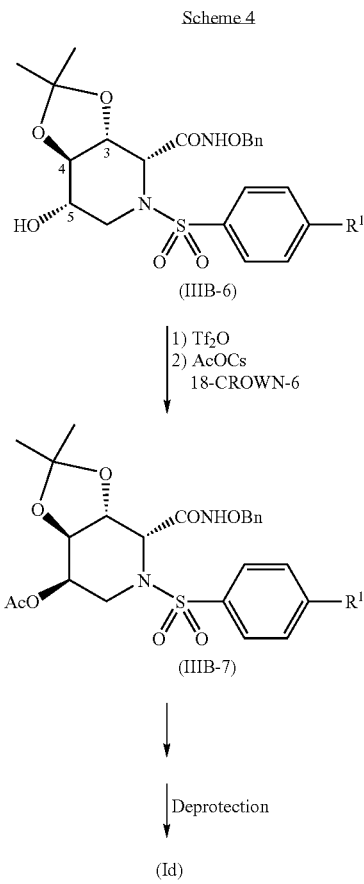

(wherein R¹ is as defined above), the stereoisomer (Id) can also be prepared by protecting hydroxyl groups at the 3- and 4-positions of the stereoisomer (Ia) and performing steric inversion of a hydroxyl group at the 5-position (the numbering is based on the piperidine ring).

First, a compound (IIIB-7) is obtained by steric inversion of a free hydroxyl group of a compound (IIIB-6) [one of the compound (IIIB-5) in Scheme 3]. Specifically, said hydroxyl group is converted into a triflate group and then the $S_N2$ nucleophilic substitution reaction due to acetoxy ions is conducted. The reaction conditions are the same as in Scheme 2.

Subsequently, the respective protective groups, for example, an acetyl group, an acetonide group and a benzyl group of the compound (IIIB-7) are cleaved and removed in any order to obtain the objective stereoisomer (Id). The reaction conditions are the same as in Scheme 1.

These compounds can be orally or parenterally administered to human.

The pharmaceutical preparations for oral administration include solid preparations such as tablets, granules, powders, fine granules and hard capsules, and solutions such as syrups and soft capsules. These preparations can be prepared by a conventional method. For example, tablets, granules, powders or fine granules are prepared by mixing the above compound or pharmaceutically acceptable salt thereof with a conventional pharmaceutically acceptable carrier, such as lactose, starch, crystalline cellulose, magnesium stearate, hydroxypropyl cellulose, talc, etc., and the hard capsules can be prepared by filling the above fine granules or powders into suitable capsules. Besides, the syrups are prepared by dissolving or suspending the above compound or pharmaceutically acceptable salt thereof in an aqueous solution containing sucrose, carboxycellulose, etc., and the soft capsules are prepared by dissolving or suspending the compound or pharmaceutically acceptable salt thereof in lipid excipients (for example, vegetable oils, oily emulsion, glycol, etc.) and then filling the resultant into soft capsules.

The pharmaceutical preparations suitable for parenteral administration include injections and further percutaneous preparations (ointment, lotion or cream preparation), suppositories (for example, suppository for rectal administration, suppository for vaginal administration), and nasal preparation (for example, spray preparation). These preparations can be prepared by a conventional method. For example, the injections can be prepared by dissolving or emulsifying the compound or pharmaceutically acceptable salt thereof in physiological saline or a lipid excipient (for example, vegetable oil, oily emulsion, glycol, etc.) and then filling in an ampoule or vial with sealing under sterile condition. Ointment preparation is prepared by mixing the above compound or pharmaceutically acceptable salt thereof with a base such as vaseline, paraffin or glycerin, and optionally adding an emulsifier or a preservative by a conventional method.

The dosage of the drug of the present invention may vary depending on the dosage forms, ages, sexes, weights or conditions of the patients, but it is usually in the range of 0.1–600 mg/kg weight/day, and preferably 10–200 mg/kg weight/day of the active ingredient, which is administered once a day or divided into 2 to 4 dosage units.

TEST EXAMPLE 1

1. Test Compound
   Compound a: Example 2
   Compound b: Example 3
   Compound c: Example 4
   Compound d: Example 1
   Compound e: Example 5

2. Test Method

Human fibrosarcoma HT-1080 transfectant expressing fusion protein of HB-EGF and human placental alkaline phosphatase (AP) were used for following tests.

The cultured transfectant was treated with Trypsin-EDTA solution, and suspended in Minimum Essential Medium without phenol red; supplemented with 10% FCS(hereinafter referred to as MEM) at the concentration of $1.0 \times 10^5$ cells/ml. Each 0.2 ml of the cell suspension was dispensed into individual wells of 96 well microplate, and incubated overnight in a $CO_2$ incubator at 37° C. After the incubation, the culture supernatant was removed by suction and the wells were washed with 0.2 ml/well of phosphate buffered saline. The cells were pretreated with 0.1 ml/well of the test compound solution [prepared by diluting a 1 mM or 0.1 mM dimethyl sulfoxide (hereinafter referred to as DMSO) solution with DMSO and further diluting 100 times with MEM to necessary consentration] for 30 min in a $CO_2$ incubator at 37° C. Then the culture supernatant was removed by suction and cells were treated with 0.2 ml/well of TPA solution (120 μM of DMSO solution was diluted to 60 nM with MEM) containing the same concentration of the compound as pretreatment for 60 min in a $CO_2$ incubator at 37° C. The cells pretreated with MEM and incubated with only the TPA solution containing no test compound were used as control.

After these treatments, each 0.1 ml of culture supernatant collected from each well and 0.1 ml of MEM as background were transferred to individual wells of new 96 well microplate and incubated at 65° C. for 10 min after plate sealing to inactivate endogenous AP in MEM and cells. 0.1 ml of the substrate solution (prepared by diluting an aqueous 100 mg/ml p-nitrophenyl phosphate solution prepared previously 100 times with 0.01% magnesium chloride/1 M diethanolamine before use) for AP was added to each well and incubated for 120 minutes at room temperature in the dark. The absorbance at a wavelength of 405 nm of each well was measured using a microplate reader. The IC50 (μM) values of the test compounds were calculated by determining the concentration of the test compounds required to exhibit 50% of the absorbance, a difference between absorbance of the well containing only MEM as background and absorbance of the culture supernatant in case of adding only TPA being 100.

3. Test Results

The test results are shown in Table 1.

TABLE 1

| Test compounds | IC50 (μM) |
|---|---|
| Compound a | 0.61 |
| Compound b | 0.45 |
| Compound c | 0.35 |
| Compound d | 1.6 |
| Compound e | 0.34 |

TEST EXAMPLE 2

1. Test Compound
   Compound c (Example 4):

2. Test Method

After backs of male BALB/c mice were shaved, 10 μL of a TPA-acetone solution (0.1 mM) was applied to the dorsal skin surface in an area of about 1 cm². In the medicine-treated group, a volume of 20 μL of a solution prepared by dissolving the test compound in acetone was applied to the same area 5 minutes, 24 hours and 48 hours after TPA application. In the non-treated group, only TPA was applied. In the control group, acetone was applied instead of the TPA-acetone solution.

The mice were sacrificed and the skin tissues were excised 72 hours after TPA application. Then the tissues were fixed with formalin, the vertical sections including the center of the TPA- or acetone-treated area were prepared and embedded in paraffin according to the conventional method. And they were stained by hematoxylin-eosin after removing paraffin. The epidermal thickness was measured using a microscope.

The epidermal thickness of the group treated with TPA and the test compounds (the treated group) was compared with those of the non-treated group and the control group, and thus hyperplasia inhibitory activity of the test compounds was examined.

3. Test Results

The test results are shown in FIG. 1. In FIG. 1, the numeral in the ordinate represents the epidermal thickness (μm). A bar graph of TPA (−) represents the epidermal thickness of the control group and a bar graph of TPA represents the epidermal thickness of the non-treated group. The respective bar graphs of 1, 10 and 100 denote the epidermal thickness of the group wherein the test compound is administered at a dose of 1, 10 and 100 (μg/wound) of each test compound. A significance test of the treated group relative to the non-treated group was conducted by the Dunnett's method. The results are indicated by the symbol * or ** (* p<0.05, ** p<0.01). A longitudinal bar represents standard error.

TEST EXAMPLE 3

1. Test Compound

Compound c (Example 4):

2. Test Method

Wound healing model was prepared in accordance with the method described by Tsuboi, et al. (J. Dermatol., 19, 673–675 (1992)). After backs of male BALB/c mice were shaved, two full-thickness round wounds (6 mm diameter) were prepared on the back of each mouse using a punch biopsy instrument. In medicine-treated group, immediately after the operation, a test compound suspended in 0.01M phosphate-buffered saline containing 1.5% sodium carboxymethyl cellulose (vehicle) was applied to each wound in a volume of 50 μL/wound. From the following day, the compound was repeatedly applied to each wound once a day for 7 days. In the control group, vehicle solution only was applied in the same manner. Eight days after the operation, mice were sacrificed and skin tissues containing wound area were removed. The tissues were fixed with a 10% neutral buffer formalin solution for one day and embedded in paraffin according to the conventional method. The cross-sections were made perpendicularly to the anterior-posterior axis. Keratinocytes in the specimen were stained by immuno histochemical staining method with an anti-keratin antibody after removing paraffin. Measurements of wound size (mm) and re-epithelialization of keratinocytes (mm) were performed by using an image-analyzing software. Re-epithelialization rate(%) of keratinocytes was calculated as follows with regard to each animal.

Re-epithelialization rate (%) of Keratinocytes=[(Re-epithelialization of Keratinocytes)/(Wound Size)]×100

3. Test Results

Figure 2:
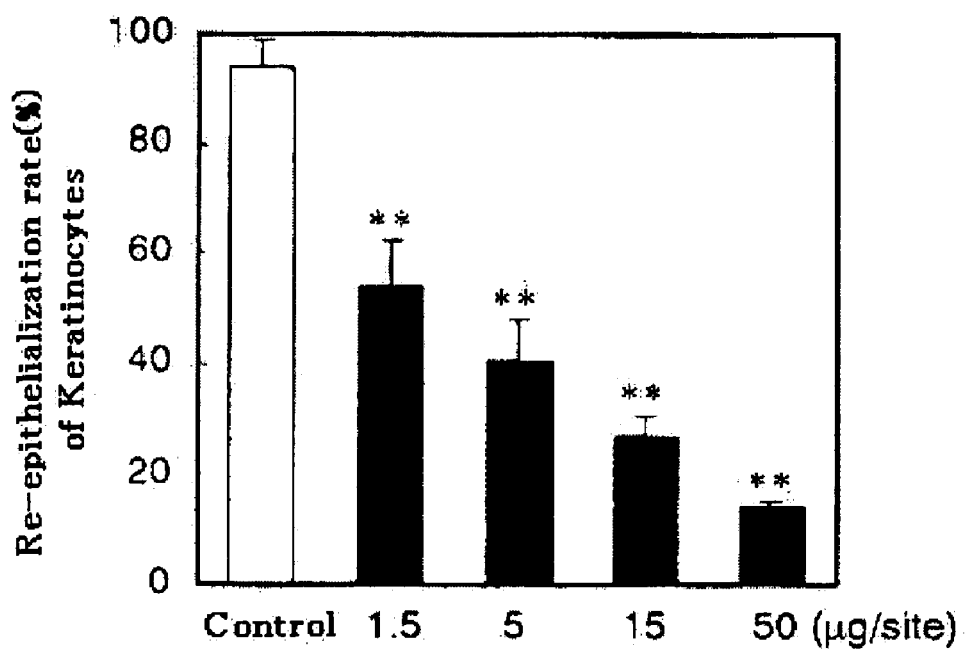
FIG. 2 is a graph showing re-epithelialization rate (%) of keratinocytes inhibitory activity by virtue of a compound of Example 4.

The test results are shown in FIG. 2. In FIG. 2, the numeral in the ordinate represents re-epithelialization rate (%) of keratinocytes. Black four bar graphs denote re-epithelialization rate (%) of keratinocytes of the treated group and the numeral at the bottom represents a dose (μg/wound) of each test compound. The bar graph of control represents re-epithelialization rate (%) of keratinocytes of the control group. A significance test of the treated group relative to the control group was conducted by the Dunnett's method. The results are indicated by the symbol  ( p<0.01). A longitudinal bar represents standard error.

The present invention will now be described in more detail by way of examples. The intermediates described in Examples 6 to 9 can be converted into a final compound (I) in the same manner as in Examples 1 to 5.

EXAMPLE 1

Preparation of (2R,3S,4R,5S)-3,4,5-trihydroxy-1-(4'-methoxybenzenesulfonyl)-piperidine-2-carboxylic Acid Hydroxamide (1) (3S,4'S,5'R)-3-acetoxy-3-[5'-(tert-butyldimethyl-silanyloxymethyl)-2',2'-dimethyl-[1,3]dioxolan-4'-yl]-2-(4"-methoxybenzenesulfonylamino)-propionic Acid Benzyl ester

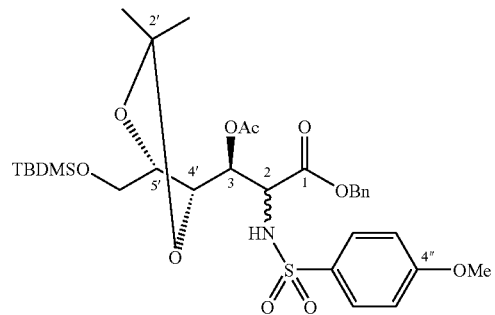

A known compound (IVa) [compound of the general formula (IV) wherein $R^1$ is a methoxy group and an acetoxy group at the 3-position is a hydroxyl group, 20.0 g] was dissolved in pyridine (80 mL) and acetic anhydride (40 mL) was added, and then the mixture was stirred at room temperature for 3 hours. Methanol (20 mL) was added and, after stirring for 5 minutes, the solvent was concentrated under reduced pressure. After the resulting residue was dissolved in ethyl acetate (300 mL) and washed with 2.5% citric acid (×2) and water, the organic layer was dried over magnesium sulfate and the solvent was distilled off under reduced pressure. The resulting residue was purified by silica gel medium pressure column chromatography (ethyl acetate:cyclohexane=1:5→1:4) to obtain the titled compound (16.2 g) as a syrup.

$^1$H-NMR(CDCl$_3$) δ: 0.07 (s), 0.10 (s), 0.85–1.0 (m), 1.2–1.4 (m), 1.44 (s), 1.96 (s), 2.07 (s), 3.5–4.0 (m), 4.1–4.2 (m), 4.40 (dd, J=1.9, 10.7 Hz), 4.48 (dd, J=2.6, 8.9 Hz), 4.8–5.3 (m), 5.56 (d, J=9.0 Hz), 6.8–6.9 (m), 7.1–7.45 (m), 7.7–7.8 (m).

(2) (2R,3S,4'S,5'S)-3-acetoxy-3-[5'-hydroxymethyl-2',2'-dimethyl-[1,3]dioxolan-4'-yl]-2-(4"-methoxy-benzenesulfonylamino)-propionic Acid Benzyl Ester

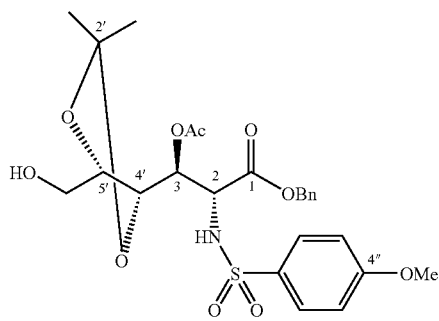

The above compound (1) (16.0 g) was dissolved in THF (200 mL) and acetic acid (4.06 g) was added and also TBAF (67.2 mL) was added under ice-cool stirring, and then the mixture was stirred at room temperature for 1.5 hours. To the reaction solution was added ethyl acetate (300 mL) and, after washing with water and saturated saline, the solution was dried over magnesium sulfate and the solvent was distilled off under reduced pressure. The resulting residue was purified by silica gel medium pressure column chromatography (ethyl acetate:cyclohexane=1:3→1:2→1:1→3:2→2:1) to obtain the titled compound (4.17 g) as a syrup.

$^1$H-NMR(CDCl$_3$) δ: 1.22 (s, 3H), 1.36 (s, 3H), 2.07 (s, 3H), 3.5–3.7 (m, 1H), 3.75–3.9 (m, 1H), 3.86 (s, 3H), 3.9–4.2 (m, 2H), 4.47 (dd, 1H, J=2.7, 8.9 Hz), 4.90 (d, 1H, J=12.2 Hz), 5.09 (d, 1H, J=12.2 Hz), 5.14 (dd, 1H, J=2.6, 8.8 Hz), 5.55 (d, 1H, J=8.8 Hz), 6.89 (d, 2H, J=8.9 Hz), 7.2–7.4 (m, 5H), 7.73 (d, 2H, J=8.9 Hz).

(3) (3aS,6R,7S,7aS)-7-acetoxy-5-(4'-methoxybenzenesulfonyl)-2,2-dimethyl-hexahydro-[1,3]dioxolo[4,5-c]pyridine-6-carboxylic Acid Benzyl Ester

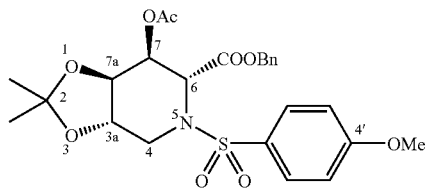

The above compound (2) (4.1 g) was dissolved in THF (50 mL) and triphenylphosphine (3.0 g) was added and, after ice cooling, DEAD (2.0 g) was added and the mixture was stirred at room temperature for 40 minutes. To the reaction solution was added ethyl acetate (150 mL) and, after washing with saturated saline, the solution was dried over magnesium sulfate and the solvent was distilled off under reduced pressure. The resulting residue was purified by silica gel medium pressure column chromatography (ethyl acetate:n-hexane=1:3) to obtain the titled compound (2.7 g) as a syrup.

$^1$H-NMR(CDCl$_3$) δ: 1.35 (s, 3H), 1.41 (s, 3H), 2.13 (s, 3H), 3.15 (dd, 1H, J=11.1, 11.9 Hz), 3.27 (dd, 1H, J=2.5, 9.3 Hz), 3.86 (s, 3H), 3.9–4.0 (m, 1H), 4.15–4.25 (m, 1H), 5.12 (d, 1H, J=12.0 Hz), 5.18 (d, 1H, J=12.0 Hz), 5.2–5.25 (m, 1H), 5.81 (t, 1H, J=2.5 Hz), 6.88 (d, 2H, J=9.0 Hz), 7.25–7.4 (m, 5H), 7.71 (d, 2H, J=9.0 Hz).

(4) (3aS,6R,7S,7aS)-7-acetoxy-5-(4'-methoxybenzenesulfonyl)-2,2-dimethyl-hexahydro-[1,3]dioxolo[4,5-c]pyridine-6-carboxylic Acid Benzyloxyamide

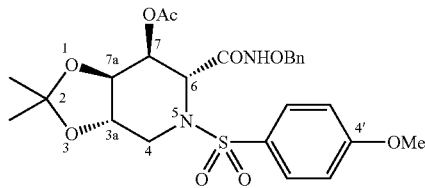

The above compound (3) (2.7 g) was dissolved in ethyl acetate (50 mL) and 10% Pd—C (270 mg) was added, and then the mixture was stirred under a hydrogen atmosphere at room temperature for one hour. The catalyst was removed by filtration and the filtrate was concentrated under reduced pressure. The resulting residue was dissolved in DMF (30 mL) and WSC (1.3 g) and HOBt (913 mg) were added. Subsequently, benzylhydroxylamine hydrochloride (1.08 g) and DIEA (873 mg) were added, followed by stirring at room temperature for 3 hours. Furthermore, WSC (299 mg), HOBt (211 mg), benzylhydroxylamine hydrochloride (248 mg) and DIEA (202 mg) were added, followed by stirring for 45 minutes. To the reaction solution was added ethyl acetate (200 mL) and, after washing in turn with 0.5N hydrochloric acid, aqueous saturated sodium hydrogencarbonate solution and saturated saline, the solution was dried over magnesium sulfate and the solvent was distilled off under reduced pressure. The resulting residue was purified by silica gel medium pressure column chromatography (ethyl acetate:n-hexane=1:3→1:2→2:3) to obtain the titled compound (2.08 g) as a syrup.

$^1$H-NMR(CDCl$_3$) δ: 1.37 (s, 3H), 1.41 (s, 3H), 1.88 (s, 3H), 3.0–3.2 (m, 1H), 3.5–3.7 (m, 2H), 3.89 (s, 3H), 4.2–4.3 (m, 1H), 4.73 (bs, 1H), 4.89 (d, 1H, J=11 Hz), 4.96 (d, 1H, J=11 Hz), 5.71 (t, 1H, J=2.1 Hz), 6.98 (d, 1H, J=9.0 Hz), 7.42 (s, 5H), 7.71 (d, 2H, J=9.0 Hz).

(5) (3aS,6R,7S,7aS)-7-hydroxy-5-(4'-methoxybenzenesulfonyl)-2,2-dimethyl-hexahydro-[1,3]dioxolo[4,5-c]pyridine-6-carboxylic Acid Benzyloxyamide

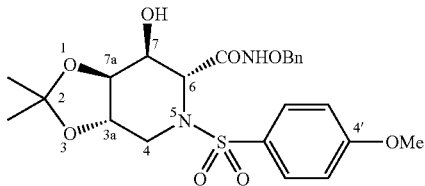

The above compound (4) (1.85 g) was dissolved in methanol (25 mL) and 28% NaOMe (668 mg) was added, and then the mixture was stirred at room temperature for 2 hours. Furthermore, 28% NaOMe (334 mg) was added and, after stirring at room temperature for 3 hours, the reaction solution was mixed with ethyl acetate (150 mL) and then washed with 0.5N hydrochloric acid and saturated saline. The organic layer was dried over magnesium sulfate and the solvent was distilled off under reduced pressure, and then the resulting residue was purified by silica gel medium pressure column chromatography (ethyl acetate:cyclohexane=2:3) to obtain the titled compound (1.36 g) as a syrup.

$^1$H-NMR(CDCl$_3$) δ: 1.32 (s, 3H), 1.39 (s, 3H), 3.02 (dd, 1H, J=10.9, 12.8 Hz), 3.3–3.55 (m, 2H), 3.88 (s, 3H), 4.07 (dd, 1H, J=4.1, 12.8 Hz), 4.75–5.05 (m, 4H), 6.96 (d, 2H, J=9.1 Hz), 7.3–7.5 (m, 5H), 7.80 (d, 2H, J=9.1 Hz), 9.17 (s, 1H).

(6) (2R,3S,4R,5S)-3,4,5-trihydroxy-1-(4'-methoxy-benzenesulfonyl)-piperidine-2-carboxylic Acid Benzyloxyamide

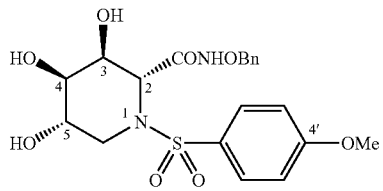

The above compound (5) (1.1 g) was dissolved in methanol (25 mL) and a cation exchange resin (Muromac, 3.0 g) was added, and then the mixture was stirred overnight at room temperature. The insoluble material was removed by filtration and the filtrate was concentrated under reduced pressure. The resulting residue was purified by silica gel medium pressure column chromatography (chloroform:methanol=20:1) to obtain the titled compound (974 mg) as a syrup.

$^1$H-NMR(DMSO-d$_6$) δ: 3.16 (d, 1H, J=5.0 Hz), 3.4–3.7 (m, 2H), 3.81 (s, 3H), 4.27 (d, 1H, J=2.1 Hz), 4.68 (s, 2H), 4.86 (d, 1H, J=5.4 Hz), 4.94 (d, 1H, J=4.5 Hz), 5.05 (d, 1H, J=3.8 Hz), 7.07 (d, 2H, J=8.9 Hz), 7.25–7.5 (m, 5H), 7.71 (d, 2H, J=8.9 Hz), 11.5 (s, 1H).

(7) (2R,3S,4R,5S)-3,4,5-trihydroxy-1-(4'-methoxy-benzenesulfonyl)-piperidine-2-carboxylic Acid Hydroxamide

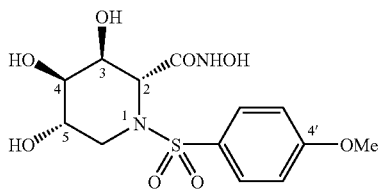

The above compound (6) (316 mg) was dissolved in methanol (25 mL) and 10% Pd—C (40 mg) was added, and then the mixture was stirred under a hydrogen atmosphere at room temperature for 2 hours. The catalyst was removed by filtration and the filtrate was concentrated under reduced pressure to obtain the titled compound (242 mg) as a colorless powder.

$^1$H-NMR(DMSO-d$_6$) δ: 3.25–3.7 (m, 5H), 3.83 (s, 3H), 4.34 (d, 1H, J=2.0 Hz), 4.7–5.2 (m, 3H), 7.05 (d, 2H, J=8.9 Hz), 7.72 (d, 2H, J=8.9 Hz), 8.88 (s, 1H), 10.86 (s, 1H). TOF-Mass: 385 (M+Na).

EXAMPLE 2

Preparation of (2R,3R,4R,5S)-3,4,5-trihydroxy-1-(4'-methoxybenzenesulfonyl)-piperidine-2-carboxylic Acid Hydroxamide

(1) (2R,4'S,4"S,5'R)-(4-methoxybenzenesulfonylamino)-(2',2',2",2"-tetramethyl-[4',4"]bis[[1,3]dioxolanyl]-5'-yl)-acetic Acid Methyl Ester

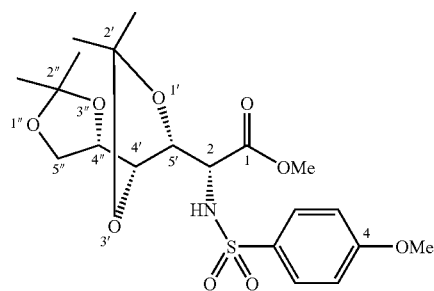

A known compound [(2R,4'S,4"S,5'R)-azide-(2',2',2",2"-tetramethyl-[4',4"]bis[[1,3]dioxolanyl]-5'-yl)-acetic acid methyl ester, 18.7 g] was dissolved in ethyl acetate (180 mL) and 10% Pd—C (3.0 g) was added, and then the mixture was stirred under a hydrogen pressure at room temperature for 4 hours. The catalyst was removed by filtration and the filtrate was concentrated under reduced pressure. The resulting residue was dissolved in DMF (160 mL) and DMAP (8.7 g) and p-methoxybenzenesulfonyl chloride (14.7 g) were added, followed by stirring at room temperature for 12 hours. To the reaction solution was added ethyl acetate (500 mL) and, after washing in turn with 1N hydrochloric acid, water and saturated saline, the organic layer was dried over magnesium sulfate and the solvent was distilled off under reduced pressure. The resulting residue was purified by silica gel medium pressure column chromatography (ethyl acetate:n-hexane=2:3) to obtain the titled compound (22.0 g) as a syrup.

$^1$H-NMR(CDCl$_3$) δ: 1.37 (s, 3H), 1.39 (s, 3H), 1.42 (s, 3H), 1.43 (s, 3H), 3.56 (s, 3H), 3.86 (s, 3H), 3.85–4.3 (m, 6H), 5.36 (d, 1H, J=10.1 Hz), 6.96 (d, 2H, J=9.0 Hz), 7.76 (d, 2H, J=9.0 Hz).

(2) (1"S,2R,4'R,5'S)-[5'-(1",21'-dihydroxy-ethyl)-2',2'-dimethyl-[1,3]dioxolan-4'-yl]-(4-methoxybenzenesulfonylamino)-acetic Acid Methyl Ester

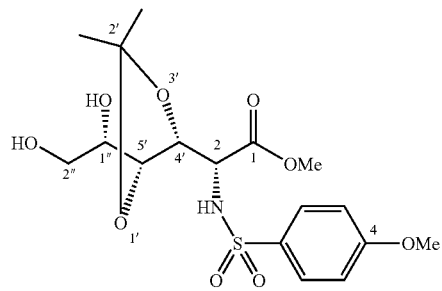

The above compound (1) (18.9 g) was dissolved in 90% aqueous methanol (450 mL) and a cation exchange resin (Muromac, 16.1 g) was added, and then the mixture was stirred at room temperature for 3 days. The insoluble material was removed by filtration and the filtrate was concentrated under reduced pressure. The resulting residue was purified by silica gel medium pressure column chromatography (ethyl acetate:n-hexane=2:3→chloroform:methanol=40:1) to obtain the titled compound (10.5 g), and a starting material (6.9 g) was recovered.

$^1$H-NMR(CDCl$_3$) δ: 1.37 (s, 3H), 1.42 (s, 3H), 3.56 (s, 3H), 3.7–3.8 (m, 3H), 3.86 (s, 3H), 3.99 (dd, 1H, J=1.6, 9.7 Hz), 4.20 (dd, 1H, J=2.0, 8.4 Hz), 4.39 (dd, 1H, J=1.7, 8.4 Hz), 5.53 (d, 1H, J=9.8 Hz), 6.95 (d, 2H, J=9.0 Hz), 7.75 (d, 2H, J=9.0 Hz).

(3) (1″R,2R,4′R,5′S)-[5′-(1″-hydroxy-21′-methanesulfonyloxy-ethyl)-2′,2′-dimethyl-[1,3]dioxolan-4′-yl]-(4-methoxybenzenesulfonylamino)-acetic Acid Methyl Ester

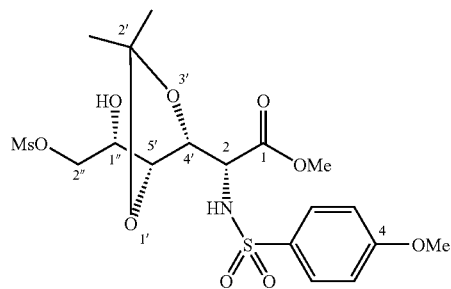

The above compound (2) (3.3 g) was dissolved in methylene chloride (50 mL) and triethylamine (1.11 mL) was added and, after cooling to −40° C., mesyl chloride (0.62 mL)/methylene chloride (3 mL) was slowly added dropwise and the mixture was stirred at the same temperature for 50 minutes. The reaction solution was washed with saturated saline and the organic layer was dried over magnesium sulfate, and then the solvent was distilled off under reduced pressure. The resulting residue was purified by silica gel medium pressure column chromatography (ethyl acetate:n-hexane=1:2→2:3→1:1) to obtain the titled compound (1.74 g).

$^1$H-NMR(CDCl$_3$) δ: 1.38 (s, 3H), 1.43 (s, 3H), 2.60 (d, 1H, J=8.0 Hz), 3.14 (s, 3H), 3.58 (s, 3H), 3.87 (s, 3H), 3.95–4.1 (m, 2H), 4.25–4.5 (m, 4H), 5.42 (d, 1H, J=9.6 Hz), 6.97 (d, 2H, J=9.0 Hz), 7.76 (d, 2H, J=9.0 Hz).

(4) (3aR,4R,7S,7aR)-7-hydroxy-5-(4′-methoxybenzenesulfonyl)-2,2-dimethyl-hexahydro-[1,3]dioxolo[4,5-c]pyridine-4-carboxylic Acid Methyl Ester

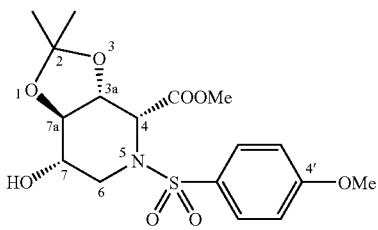

The above compound (3) (4.6 g) was dissolved in DMF (150 mL) and potassium carbonate (1.54 g) was added, and then the mixture was stirred at 45° C. for 1.5 hours. To the reaction solution was added ethyl acetate (300 mL) and, after washing with water (×2) and saturated saline, the organic layer was dried over magnesium sulfate and the solvent was distilled off under reduced pressure. The resulting residue was purified by silica gel medium pressure column chromatography (ethyl acetate:n-hexane=2:3→1:1) to obtain the titled compound (3.1 g) as a syrup.

$^1$H-NMR(CDCl$_3$) δ: 1.35 (s, 3H), 1.45 (s, 3H), 2.41 (d, 1H, J=4.1 Hz), 3.25 (dd, 1H, J=9.6, 12.0 Hz), 3.58 (s, 3H), 3.5–3.65 (m, 1H), 3.7–3.8 (m, 1H), 3.88 (s, 3H), 3.9–4.2 (m, 2H), 5.06 (d, 1H, J=6.1 Hz), 6.98 (d, 2H, J=9.0 Hz), 7.70 (d, 2H, J=9.0 Hz).

(5) Preparation of (3aS,6R,7R,7aS)-7-hydroxy-5-(4′-methoxybenzenesulfonyl)-2,2-dimethyl-hexahydro-[1,3]dioxolo[4,5-c]pyridine-6-carboxylic Acid Benzyloxyamide

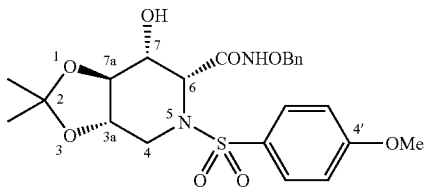

(5-1) (3aS,6R,7R,7aS)-7-hydroxy-5-(4′-methoxybenzenesulfonyl)-2,2-dimethyl-hexahydro-[1,3]dioxolo[4,5-c]pyridine-6-carboxylic Acid Methyl Ester The above compound (4) (780 mg) was dissolved in methanol (15 mL) and a cation exchange resin (Muromac, 5.0 g) was added, and then the mixture was stirred at room temperature for 6.5 hours. The insoluble material was removed by filtration and the filtrate was concentrated under reduced pressure. The resulting residue was dissolved in DMF (30 mL) and DMP (1.8 g) and p-toluenesulfonic acid monohydrate (20 mg) were added, followed by stirring at room temperature for 5 hours and further stirring at 50° C. for one hour. To the reaction solution was added ethyl acetate (150 mL) and, after washing in turn with an aqueous saturated sodium hydrogencarbonate solution, water and saturated saline, the solution was dried over magnesium sulfate and the solvent was distilled off under reduced pressure. The resulting residue was purified by silica gel medium pressure column chromatography (ethyl acetate:n-hexane=2:3→1:1) to obtain a mixture (620 mg) of the -titled compound and the above compound (4).

(5-2) (3aS,6R,7R,7aS)-7-hydroxy-5-(4′-methoxybenzenesulfonyl)-2,2-dimethyl-hexahydro-[1,3]dioxolo[4,5-c]pyridine-6-carboxylic Acid Benzyloxyamide The above mixture (5-1) (620 mg) was dissolved in methanol (30 mL) and an aqueous 1N sodium hydroxide solution (8.5 mL) was added, and then the mixture was stirred at room temperature for 5 hours. To the reaction solution was added water (50 mL) and, after washing with ether, the aqueous layer was acidified with an aqueous 10% citric acid solution and then extracted with ethyl acetate. The organic layer was washed with water and saturated saline, dried over magnesium sulfate, and then the solvent was distilled off under reduced pressure. The resulting residue was dissolved in DMF (30 mL) and WSC (431 mg) and HOBt (344 mg) were added. Subsequently, benzylhydroxylamine hydrochloride (359 mg) and DIEA (291 mg) were added, followed by stirring overnight at room temperature. To the reaction solution was added ethyl acetate (100 mL) and, after washing in turn with an aqueous 10% citric acid solution, an aqueous saturated sodium hydrogencarbonate solution, water and saturated saline, the solution was dried over magnesium sulfate and the solvent was distilled off under reduced pressure. The resulting residue was purified by silica gel medium pressure column chromatography (ethyl acetate:cyclohexane=2:3→1:1) and the precipitated solid material was collected by filtration to obtain the titled compound (98 mg).

$^1$H-NMR(CDCl$_3$) δ: 1.36 (s, 3H), 1.41 (s, 3H), 2.9–3.2 (m, 2H), 3.55–3.75 (m, 2H), 3.88 (s, 3H), 4.1–4.25 (m, 2H), 4.68 (d, 1H, J=4.3 Hz), 6.98 (d, 2H, J=9.0 Hz), 7.73 (d, 2H, J=9.0 Hz), 9.1 (s, 1H).

(6) Preparation of (2R,3R,4R,5S)-3,4,5-trihydroxy-1-(4'-methoxybenzenesulfonyl)-piperidine-2-carboxylic Acid Benzyloxyamide

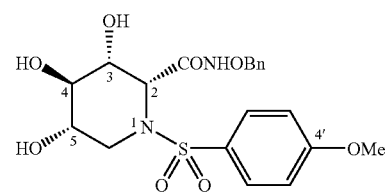

The above compound (5-2) (100 mg) was dissolved in a solvent mixture of 1,4-dioxane/methanol (5–15 mL) and a cation exchange resin (Muromac, 2.5 g) was added, and then the mixture was stirred at room temperature for 14 hours. The insoluble material was removed by filtration and the filtrate was concentrated under reduced pressure. The resulting residue was purified by silica gel medium pressure column chromatography (chloroform:methanol=20:1→10:1) to obtain the titled compound (88 mg).

$^1$H-NMR(DMSO-d$_6$+D$_2$O) δ: 3.0–3.25 (m, 1H), 3.28 (dd, 1H, J=6.7, 9.4 Hz), 3.41 (t, 1H, J=11.1 Hz), 3.81 (s, 3H), 4.17 (d, 1H, J=6.8 Hz), 4.49 (d, 1H, J=10.6 Hz), 4.57 (d, 1H, J=10.6 Hz), 7.07 (d, 2H, J=8.9 Hz), 7.25–7.45 (m, 5H), 7.67 (d, 2H, J=8.9 Hz).

(7) (2R,3R,4R,5S)-3,4,5-trihydroxy-1-(4'-methoxybenzenesulfonyl)-piperidine-2-carboxylic Acid Hydroxamide

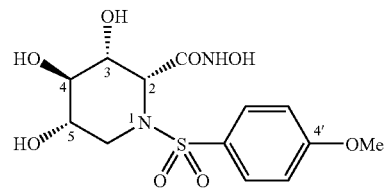

The above compound (6) (88 mg) was dissolved in methanol (12 mL) and 10% Pd—C (20 mg) was added, and the mixture was stirred under a hydrogen atmosphere at room temperature for 2 hours. After the catalyst was removed by filtration and the filtrate was concentrated under reduced pressure, the resulting residue was freeze-dried to obtain the titled compound (60 mg) as a colorless amorphous.

$^1$H-NMR(DMSO-d$_6$) δ: 3.0–3.7 (m, 5H), 3.84 (s, 3H), 4.20 (d, 1H, J=5.3 Hz), 7.09 (d, 2H, J=9.0 Hz), 7.67 (d, 2H, J=9.0 Hz), 8.82 (bs, 1H), 10.67 (s, 1H). TOF-Mass: 385 (M+Na), 401 (M+K).

EXAMPLE 3

Preparation of (2R,3R,4R,5S)-1-(4'-ethoxyethoxybenzenesulfonyl)-3,4,5-trihydroxy-piperidine-2-carboxylic Acid Hydroxamide (1) (2R,4'S,4"S,5'R)-(4-(ethoxyethoxy)benzenesulfonylamino]-(2',2',2",2"-tetramethyl-[4',4"]bis[[1,3]dioxolanyl]-5'-yl)-acetic Acid Methyl Ester

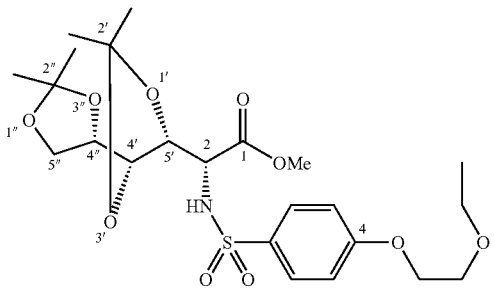

A known compound [(2R,4'S,4"S,5'R)-azide-(2',2',2",2"-tetramethyl-[4',4"]bis[[1,3]dioxolanyl]-5'-yl)-acetic acid methyl ester, 30.6 g] was dissolved in ethyl acetate (360 mL)

and 10% Pd—C (5.3 g) was added, and then the mixture was stirred under a hydrogen pressure at room temperature for 4 hours. The catalyst was removed by filtration and the filtrate was concentrated under reduced pressure. The resulting residue was dissolved in DMF (180 mL) and DMAP (14.2 g) was added and also p-ethoxyethoxybenzenesulfonyl chloride (26.3 g) was added under ice-cool stirring, followed by stirring at room temperature for 2 hours. To the reaction solution was added ethyl acetate (500 mL) and, after washing in turn with 1N hydrochloric acid, an aqueous saturated sodium hydrogencarbonate solution, water and saturated saline, the organic layer was dried over magnesium sulfate and the solvent was distilled off under reduced pressure. The resulting residue was purified by silica gel medium pressure column chromatography (ethyl acetate:n-hexane=35:65→2:3) to obtain the titled compound (35.5 g) as a syrup.

$^1$H-NMR(CDCl$_3$) δ: ••25 (t, 3H, J=7.0 Hz), 1.37 (s, 3H), 1.39 (s, 3H), 1.43 (s, 3H), 1.44 (s, 3H), 3.57 (s, 3H), 3.61 (q, 2H, J=7.0 Hz), 3.75–3.85 (m, 2H), 3.85–4.0 (m, 2H), 4.05–4.3 (m, 6H), 5.36 (d, 1H, J=10.0 Hz), 6.99 (d, 2H, J=9.0 Hz), 7.75 (d, 2H, J=9.0 Hz).

(2) Preparation of (1″S,2R,4′R,5′S)-[5′-(1″,2″-dihydroxy-ethyl)-2′,2′-dimethyl-[1,3] dioxolan-4′-yl]-[4-(ethoxyethoxy)benzenesulfonylamino]-acetic Acid Methyl Ester

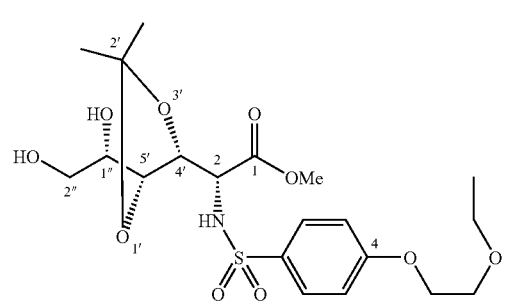

The above compound (1) (35.1 g) was dissolved in 90% aqueous methanol (800 mL) and a cation exchange resin (Muromac, 29.8 g) was added, and then the mixture was stirred at room temperature for 4 days. The insoluble material was removed by filtration and the filtrate was concentrated under reduced pressure. The resulting residue was purified by silica gel medium pressure column chromatography (ethyl acetate:n-hexane=2:3→1:1→chloroform:methanol=25:1) to obtain the titled compound (18.2 g), and a starting material (8.0 g) was recovered.

$^1$H-NMR(CDCl$_3$) δ: 1.25(t, 3H, J=7.0 Hz), 1.38 (s, 3H), 1.47 (s, 3H), 2.3 (bs, 1H), 2.66 (d, 1H, J=6.7 Hz), 3.5–3.7 (m, 5H), 3.7–3.85 (m, 5H), 3.97 (d, 1H, J=8.4 Hz), 4.1–4.25 (m, 3H), 4.40 (dd, 1H, J=1.7, 8.5 Hz), 5.46 (d, 1H, J=9.5 Hz), 6.99 (d, 2H, J=9.0 Hz), 7.75 (d, 2H, J=9.0 Hz).

(3) (1R,2R,4′R,5′S)-[4-(ethoxyethoxy)benzenesulfonylamino]-[5′-(1″-hydroxy-2″-methanesulfonyloxy-ethyl)-2′,2′-dimethyl-[1,3]dioxolan-4′-yl]-acetic Acid Methyl Ester

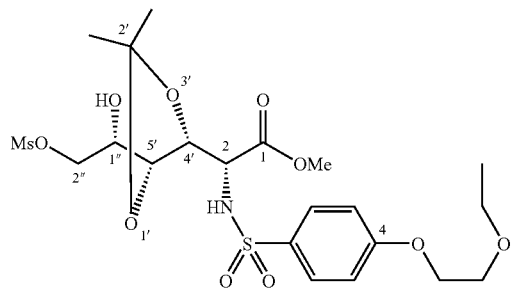

The above compound (2) (18.2 g) was dissolved in methylene chloride (300 mL) and triethylamine (4.25 g) was added and, after cooling to −60° C., mesyl chloride (4.59 g)/methylene chloride (30 mL) was slowly added dropwise and the mixture was stirred at the same temperature for 50 minutes. After the reaction solution was washed with saturated saline and the organic layer was dried over magnesium sulfate, the solvent was distilled off under reduced pressure. The resulting residue was purified by silica gel medium pressure column chromatography (ethyl acetate:cyclohexane=2:3→1:1→3:2) to obtain the titled compound (13.0 g).

$^1$H-NMR(CDCl$_3$) δ: 1.25 (t, 3H, J=7.0 Hz), 1.38 (s, 3H), 1.43 (s, 3H), 2.60 (d, 1H, J=8.0 Hz), 3.14 (s, 3H), 3.58 (q, 2H, J=7.1 Hz), 3.75–3.85 (m, 2H), 3.96 (dd, 1H, J=1.7, 9.5 Hz), 3.9–4.4 (m, 8H), 5.43 (d, 1H, J=9.5 Hz), 6.99 (d, 2H, J=9.0 Hz), 7.75 (d, 2H, J=9.0 Hz).

(4) (3aR,4R,7S,7aR)-5-(4′-ethoxyethoxy-benzenesulfonyl)-7-hydroxy-2,2-dimethyl-hexahydro-[1,3]dioxolo[4,5-c]pyridine-4-carboxylic Acid Methyl Ester

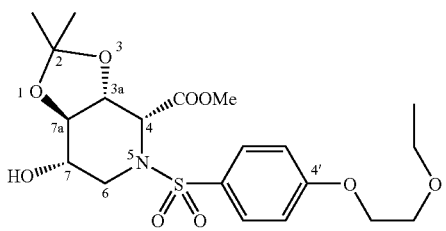

The above compound (3) (10.4 g) was dissolved in DMF (200 mL) and potassium carbonate (3.1 g) was added, and then the mixture was stirred at 50° C. for one hour. To the reaction solution was added ethyl acetate (500 mL) and, after washing with water (×2) and saturated saline, the organic layer was dried over magnesium sulfate and the solvent was distilled off under reduced pressure. The resulting residue was purified by silica gel medium pressure column chromatography (ethyl acetate:n-hexane=2:3→1:1) to obtain the titled compound (7.3 g) as a syrup.

$^1$H-NMR(CDCl$_3$) δ: 1.25 (t, 3H, J=7.0 Hz), 1.35 (s, 3H), 1.45 (s, 3H), 3.25 (dd, 1H, J=9.7, 12.1 Hz), 3.5–3.85 (m, 9H), 3.85–4.25 (m, 4H), 5.05 (d, 1H, J=6.1 Hz), 6.99 (d, 2H, J=9.0 Hz), 7.69 (d, 2H, J=9.0 Hz).

(5) Preparation of (3aS,6R,7R,7aS)-5-(4'-ethoxy-ethoxy-benzenesulfonyl)-7-hydroxy-2,2-dimethyl-hexahydro-[1,3]dioxolo[4,5-c]pyridine-6-carboxylic Acid Benzyloxyamide

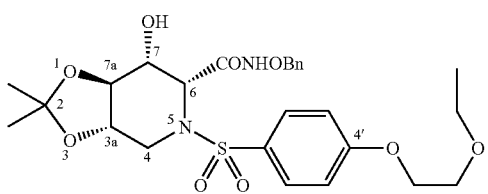

(5-1) (3aS,6R,7R,7aS)-5-(4-ethoxyethoxy-benzenesulfonyl)-7-hydroxy-2,2-dimethyl-hexahydro-[1,3]dioxolo[4,5-c]pyridine-6-carboxylic Acid Methyl Ester The above compound (4) (2.0 g) was dissolved in methanol (35 mL) and a cation exchange resin (Muromac, 8.0 g) was added, and then the mixture was stirred overnight at room temperature. The insoluble material was removed by filtration and the filtrate was concentrated under reduced pressure. The resulting residue was dissolved in DMF (15 mL) and DMP (2.7 g) and p-toluenesulfonic acid monohydrate (10 mg) were added and, after stirring overnight at room temperature, the mixture was stirred at 50° C. for one hour. To the reaction solution was added ethyl acetate (150 mL) and, after washing in turn with an aqueous saturated sodium hydrogencarbonate solution, water and saturated saline, the solution was dried over magnesium sulfate and the solvent was distilled off under reduced pressure. The resulting residue was purified by silica gel medium pressure column chromatography (ethyl acetate:n-hexane=2:3→1:1) to obtain a mixture (817 mg) of the titled compound and the above compound (4).

$^1$H-NMR(CDCl$_3$) δ: 1.25 (t, J=7.1 Hz), 1.26 (t, J=7.2 Hz), 1.35 (s), 1.43 (s), 1.45 (s), 3.07 (d, J=5.8 Hz), 3.25 (dd, J=9.7, 12.0 Hz), 3.55 (s), 3.58 (s), 3.6–3.8 (m), 3.8–4.25 (m), 4.95 (d, J=6.6 Hz), 5.05 (d, J=6.1 Hz), 7.0 (d, 2H, J=9.0 Hz), 7.69 (d, 2H, J=9.0 Hz).

(5-2) (3aS,6R,7R,7aS)-5-(4'-ethoxyethoxy-benzenesulfonyl)-7-hydroxy-2,2-dimethyl-hexahydro-[1,3]dioxolo[4,5-c]pyridine-6-carboxylic Acid Benzyloxyamide The above mixture (5-1) (817 mg) was dissolved in a solvent mixture of methanol/1,4-dioxane (5–15 mL) and an aqueous 1N sodium hydroxide solution (5 mL) was added, followed by stirring at room temperature for one hour and 20 minutes. The reaction solution was neutralized with an aqueous 5% citric acid solution and then extracted with ethyl acetate. After the organic layer was washed with water and saturated saline and dried over magnesium sulfate, the solvent was distilled off under reduced pressure. The resulting residue was dissolved in DMF (10 mL) and WSC (238 mg) and HOBt (190 mg) were added. Subsequently, benzylhydroxylamine hydrochloride (198 mg) and DIEA (160 mg) were added, followed by stirring overnight at room temperature. To the reaction solution was added ethyl acetate (100 mL) and, after washing in turn with an aqueous 10% citric acid solution, an aqueous saturated sodium hydrogencarbonate solution, water and saturated saline, the organic layer was dried over magnesium sulfate and the solvent was distilled off under reduced pressure. To the resulting residue was added ether/ethyl acetate (5:1) and the precipitated solid material was collected by filtration to obtain the titled compound (98 mg).

$^1$H-NMR(CDCl$_3$) δ: 1.25 (t, J=7.0 Hz), 1.36 (s, 3H), 1.40 (s, 3H), 2.9–3.2 (m, 2H), 3.5–3.7 (m, 4H), 3.75–3.85 (m, 2H), 4.1–4.25 (m, 4H), 4.68 (d, 1H, J=4.2 Hz), 4.88 (d, 1H, J=11.0 Hz), 4.94 (d, 1H, J=11.0 Hz), 7.01 (d, 2H, J=9.0 Hz), 7.4 (s, 5H), 7.71 (d, 2H, J=9.0 Hz), 9.10 (s, 1H).

(6) Preparation of (2R,3R,4R,5S)-1-(4'-ethoxy-ethoxy-benzenesulfonyl)-3,4,5-trihydroxy-piperidine-2-carboxylic Acid Benzyloxyamide

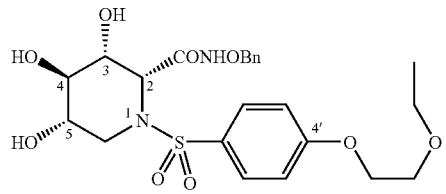

The above compound (5-2) (5.0 g) was dissolved in methanol (130 mL) and a cation exchange resin (Muromac, 23.4 g) was added, and then the mixture was stirred overnight at room temperature. The insoluble material was removed by filtration and the filtrate was concentrated under reduced pressure. The resulting residue was purified by silica gel medium pressure column chromatography (chloroform:methanol=20:1→10:1) to obtain the titled compound (4.3 g).

$^1$H-NMR(DMSO-d$_6$) δ: 1.1 (t, 3H, J=7.0 Hz), 3.0–3.2 (m, 1H), 3.25–3.3 (m, 1H), 3.35–3.75 (m, 7H), 4.54 (d, 1H, J=10.6 Hz), 4.61 (d, 1H, J=10.6 Hz), 4.98 (d, 1H, J=4.7 Hz), 5.13 (d, 1H, J=4.7 Hz), 5.44 (d, 1H, J=4.6 Hz), 7.11 (d, 2H, J=8.9 Hz), 7.35 (s, 5H), 7.69 (d, 2H, J=8.9 Hz), 11.31 (s, 1H).

(7) (2R,3R,4R,5S)-1-(4'-ethoxyethoxy-benzenesulfonyl)-3,4,5-trihydroxy-piperidine-2-carboxylic Acid Hydroxamide

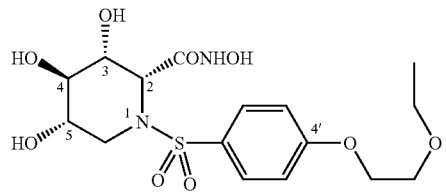

The above compound (6) (1.66 g) was dissolved in methanol (70 mL) and 10% Pd—C (350 mg) was added, and then the mixture was stirred under a hydrogen atmosphere at 40° C. for one hour. The catalyst was removed by filtration and the filtrate was concentrated under reduced pressure. The resulting residue was purified by silica gel medium pressure column chromatography (chloroform:methanol=10:1→5:1) to obtain the titled compound (815 mg) as a colorless powder.

¹H-NMR(DMSO-d₆) δ: 1.13 (t, 3H, J=7.0 Hz), 3.0–3.3 (m, 3H), 3.50 (q, 2H, J=7.0 Hz), 3.35–3.7 (m, 2H), 3.7–3.75 (m, 2H), 4.1–4.25 (m, 3H), 4.90 (d, 1H, J=4.9 Hz), 5.07 (d, 1H, J=4.7 Hz), 5.35 (d, 1H, J=4.5 Hz), 7.09 (d, 2H, J=8.9 Hz), 7.66 (d, 2H, J=8.9 Hz), 8.82 (d, 1H, J=1.95 Hz), 10.67 (d, 1H, J=1.95 Hz).

TOF-Mass: 443 (M+Na), 459 (M+K).

[α]_D 4.0° [c=0.1, MeOH]

EXAMPLE 4

Preparation of (2R,3R,4R,5S)-3,4,5-trihydroxy-1-(4'-phenoxybenzenesulfonyl)-piperidine-2-carboxylic Acid Hydroxamide (1) (2R,4'S,4"S,5'R)-(4-phenoxybenzenesulfonylamino)-(2',2',2",2"-tetramethyl-[4',4"]bis[[1,3]dioxolanyl]-5'-yl)-acetic Acid Methyl Ester

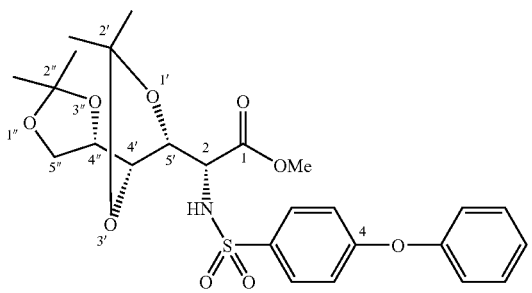

A known compound [(2R,4'S,4"S,5'R)-azide-(2',2',2",2"-tetramethyl-[4',4"]bis[[1,3]dioxolanyl]-5'-yl)-acetic acid methyl ester, 22.4 g] was dissolved in ethyl acetate (200 mL) and 10% Pd—C (2.2 g) was added, and then the mixture was stirred under a hydrogen pressure at room temperature for 4.5 hours. The catalyst was removed by filtration and the filtrate was concentrated under reduced pressure. The resulting residue was dissolved in DMF (250 mL) and DMAP (10.4 g) was added and also p-phenoxybenzenesulfonyl chloride (20.0 g) was added, followed by stirring at room temperature for 2.5 hours. To the reaction solution was added ethyl acetate (500 mL) and, after washing in turn with 1N hydrochloric acid, water and saturated saline, the organic layer was dried over magnesium sulfate and the solvent was distilled off under reduced pressure. The resulting residue was purified by silica gel medium pressure column chromatography (ethyl acetate:n-hexane=1:3→1:2) to obtain the titled compound (30.1 g) as syrup.

¹H-NMR(CDCl₃) δ: 1.39 (s, 3H), 1.40 (s, 3H), 1.44 (s, 3H), 1.45 (s, 3H), 3.62 (s, 3H), 3.9–4.3 (m, 6H), 5.39 (d, 1H, J=10.1 Hz), 7.0–7.15 (m, 4H), 7.2–7.3 (m, 1H), 7.3–7.5 (m, 2H), 7.79 (d, 2H, J=9.1 Hz).

(2) (1"S,2R,4'R,5'S)-[5'-(1",2"-dihydroxy-ethyl)-2',2'-dimethyl-[1,3]dioxolan-4'-yl]-(4-phenoxybenzenesulfonylamino)-acetic Acid Methyl Ester

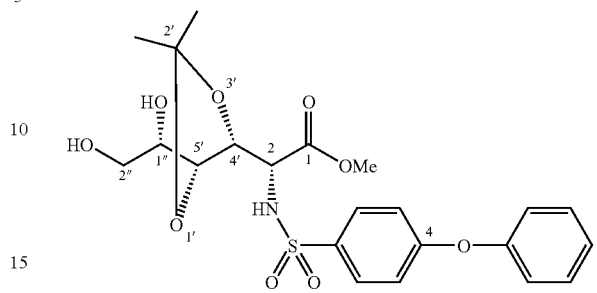

The above compound (1) (19.4 g) was dissolved in acetonitrile (230 mL) and cerium (III) chloride heptahydrate (27.7 g) and oxalic acid (167 mg) were added, and then the mixture was stirred at room temperature for 30 minutes. After neutralizing with sodium carbonate, the insoluble material was removed by filtration and washed with ethyl acetate. The filtrate and the washing were combined and concentrated under reduced pressure, and then the resulting residue was purified by silica gel medium pressure column chromatography (ethyl acetate:n-hexane=1:1→3:2→2:1) to obtain the titled compound (8.8 g), and a starting material (7.9 g) was recovered.

¹H-NMR(CDCl₃) δ: 1.40 (s, 3H), 2.15–2.25 (m, 1H), 2.61 (d, 1H, J=8.0 Hz), 3.63 (s, 3H), 3.7–3.85 (m, 3H), 4.00 (dd, 1H, J=1.7, 9.8 Hz), 4.23 (dd, 1H, J=2.4, 8.4 Hz), 4.43 (dd, 1H, J=1.7, 8.5 Hz), 5.46 (d, 1H, J=9.8 Hz), 7.0–7.15 (m, 4H), 7.2–7.3 (m, 1H), 7.35–7.5 (m, 2H), 7.78 (d, 2H, J=8.9 Hz).

(3) Preparation of (1"R,2R,4'R,5'S)-[5'-(1"-hydroxy-2"-methanesulfonyloxy-ethyl)-2',2'-dimethyl-[1,3]dioxolan-4'-yl]-(4-phenoxybenzenesulfonylamino)-acetic Acid Methyl Ester

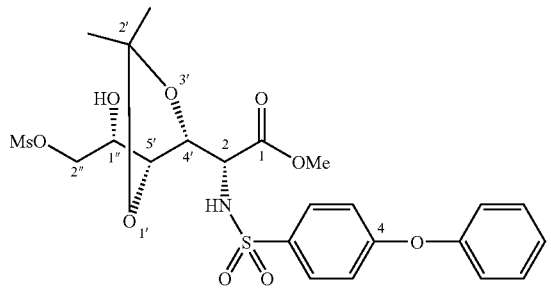

The above compound (2) (20.0 g) was dissolved in methylene chloride (180 mL) and triethylamine (4.47 g) were added and, after cooling to −40° C., mesyl chloride (4.80 g)/methylene chloride (40 mL) was slowly added dropwise and the mixture was stirred at the same temperature for 40 minutes. The reaction solution was washed with water and an aqueous saturated sodium hydrogencarbonate solution and the organic layer was dried over magnesium sulfate, and then the solvent was distilled off under reduced pressure. The resulting residue was purified by silica gel medium pressure column chromatography (ethyl acetate:n-hexane=1:3→1:2 1:1) to obtain the titled compound (14.1 g).

¹H-NMR(CDCl₃) δ: 1.39 (s, 3H), 1.44 (s, 3H), 2.57 (d, 1H, J=7.9 Hz), 3.13 (s, 3H), 3.61 (s, 3H), 3.9–4.1 (m, 2H), 4.2–4.5 (m, 4H), 5.44 (d, 1H, J=9.5 Hz), 6.95–7.15 (m, 4H), 7.15–7.35 (m, 1H), 7.35–7.5 (m, 2H), 7.77 (d, 2H, J=9.0 Hz).

(4) (3aR,4R,7S,7aR)-7-hydroxy-2,2-dimethyl-5-(4'-phenoxybenzenesulfonyl)-hexahydro-[1,3]dioxolo[4,5-c]pyridine-4-carboxylic Acid Methyl Ester

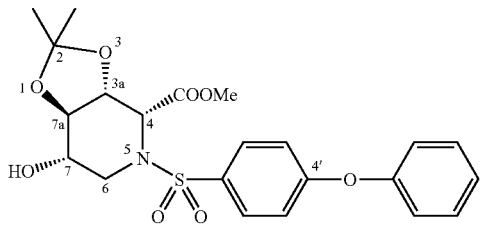

The above compound (3) (17.5 g) was dissolved in DMF (300 mL) and potassium carbonate (5.2 g) was added, and then the mixture was stirred at 50° C. for one hour and 20 minutes. To the reaction solution was added ethyl acetate (500 mL) and, after washing with water and saturated saline (×3), the organic layer was dried over magnesium sulfate and the solvent was distilled off under reduced pressure. The resulting residue was purified by silica gel medium pressure column chromatography (ethyl acetate:n-hexane=2:3) to obtain the titled compound (11.4 g) as a syrup.

¹H-NMR(CDCl₃) δ: 1.37 (s, 3H), 1.47 (s, 3H), 2.20 (d, 1H, J=4.1 Hz), 3.28 (dd, 1H, J=9.5, 11.9 Hz), 3.55–3.6 (m, 1H), 3.74 (t, 1H, J=9.2 Hz), 3.9–4.2 (m, 3H), 5.08 (d, 1H, J=6 Hz), 7.0–7.2 (m, 4H), 7.2–7.3 (m, 1H), 7.35–7.5 (m, 2H), 7.73 (d, 2H, J=9.0 Hz).

(5) Preparation of (3aS,6R,7R,7aS)-7-hydroxy-2,2-dimethyl-5-(4'-phenoxybenzenesulfonyl)-hexahydro-[1,3]dioxolo[4,5-c]pyridine-6-carboxylic Acid Benzyloxyamide

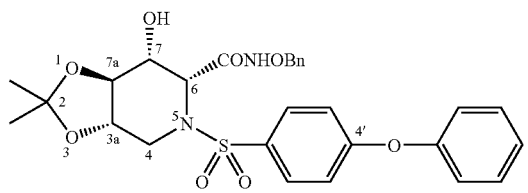

(5-1) (3aS,6R,7R,7aS)-7-hydroxy-2,2-dimethyl-5-(4'-phenoxybenzenesulfonyl)-hexahydro-[1,3]dioxolo[4,5-c]pyridine-6-carboxylic Acid Methyl Ester The above compound (4) (11.4 g) was dissolved in methanol (150 mL) and a cation exchange resin (Muromac, 25.0 g) was added, and then the mixture was stirred overnight at room temperature. The insoluble material was removed by filtration and the filtrate was concentrated under reduced pressure. The precipitated solid material was dissolved in DMF (200 mL) and DMP(20.8 g) and p-toluenesulfonic acid monohydrate (450 mg) were added and, after stirring overnight at room temperature, the mixture was stirred at 50° C. for 2 hours. To the reaction solution was added sodium hydrogencarbonate and the solvent was distilled off under reduced pressure. The resulting residue was purified by silica gel medium pressure column chromatography (ethyl acetate:n-hexane=2:3) to obtain a mixture(6.5 g) of the titled compound and the above compound (4).

(5-2) (3aS,6R,7R,7aS)-7-hydroxy-2,2-dimethyl-5-(4'-phenoxybenzenesulfonyl)-hexahydro-[1,3]dioxolo[4,5-c]pyridine-6-carboxylic Acid Benzyloxyamide The above mixture (5-1) (12.7 g) was dissolved in a solvent mixture of methanol/1,4-dioxane (30–150 mL) and an aqueous 1N sodium hydroxide solution (30 mL) was added, and then the mixture was stirred at room temperature for one hour. The reaction solution was mixed with 1N hydrochloric acid and then extracted with ethyl acetate. After the organic layer was washed with water and saturated saline and dried over magnesium sulfate, the solvent was distilled off under reduced pressure. The resulting residue was dissolved in DMF (260 mL) and WSC (10.3 g) and HOBt (8.3 g) were added. Subsequently, benzylhydroxylamine hydrochloride (8.6 g) and DIEA (7.0 g) were added, followed by stirring overnight at room temperature. To the reaction solution was added ethyl acetate (500 mL) and, after washing in turn with an aqueous 10% citric acid solution, an aqueous saturated sodium hydrogencarbonate solution, water and saturated saline, the organic layer was dried over magnesium sulfate and the solvent was distilled off under reduced pressure. To the resulting residue was added ether/ethyl acetate (5:1) and the precipitated solid material was collected by filtration to obtain the titled compound (1.28 g).

¹H-NMR(CDCl₃) δ: 1.40 (s, 3H), 1.43 (s, 3H), 3.0–3.25 (m, 2H), 3.6–3.8 (m, 2H), 4.02 (d, 1H, J=7.9 Hz), 4.17 (dd, 1H, J=3.9, 11.4 Hz), 4.71 (d, 1H, J=5.1 Hz), 4.89 (d, 1H, J=11.1 Hz), 4.95 (d, 1H, J=11.3 Hz), 7.0–7.15 (m, 3H), 7.25–7.3 (m, 3H), 7.35–7.5 (m, 6H), 7.74 (d, 2H, J=9.0 Hz), 9.07 (s, 1H).

(6) Preparation of (2R,3R,4R,5S)-3,4,5-trihydroxy-1-(4'-phenoxybenzenesulfonyl)-piperidine-2-carboxylic Acid Benzyloxyamide

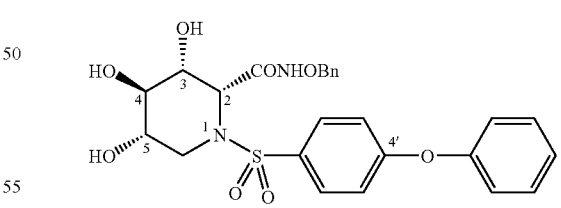

The above compound (5-2) (1.5 g) was dissolved in methanol (30 mL) and a cation exchange resin (Muromac, 3.4 g) was added, and then the mixture was stirred overnight at room temperature. The insoluble material was removed by filtration and the filtrate was concentrated under reduced pressure. The resulting residue was purified by silica gel medium pressure column chromatography (chloroform:methanol=20:1→10:1) to obtain the titled compound (1.1 g).

¹H-NMR(DMSO-d₆) δ: 3.1–3.25 (m, 1H), 3.35–3.5 (m, 3H), 4.19 (d, 1H, J=6.8 Hz), 4.53 (d, 1H, J=10.5 Hz), 4.61

(d, 1H, J=10.5 Hz), 5.01 (d, 1H, J=4.9 Hz), 5.17 (d, 1H, J=4.8 Hz), 5.49 (d, 1H, J=4.6 Hz), 7.0–7.15 (m, 4H), 7.15–7.3 (m, 1H), 7.3–7.5 (m, 7H), 7.75 (d, 2H, J=8.9 Hz), 11.32 (s, 1H).

(7) (2R,3R,4R,5S)-3,4,5-trihydroxy-1-(4'-phenoxy-benzenesulfonyl)-piperidine-2-carboxylic Acid Hydroxamide

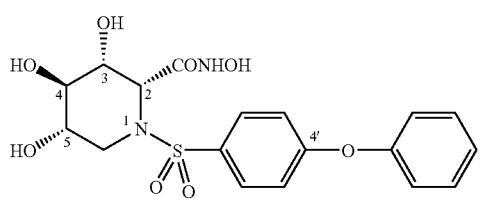

The above compound (6) (1.68 g) was dissolved in methanol (70 mL) and 10% Pd—C (350 mg) was added, and then the mixture was stirred under a hydrogen atmosphere at 40° C. for 2 hours. The catalyst was removed by filtration and the filtrate was concentrated under reduced pressure. The resulting residue was purified by silica gel medium pressure column chromatography (chloroform:methanol=20:1→9:1. 4:1) to obtain the titled compound (951 mg) as a colorless powder.

$^1$H-NMR(DMSO-$d_6$) δ: 3.0–3.7 (m, 5H), 4.20 (d, 1H, J=6.7 Hz), 4.93 (d, 1H, J=4.9 Hz), 5.11 (d, 1H, J=4.7 Hz), 5.39 (d, 1H, J=4.5 Hz), 7.0–7.25 (m, 4H), 7.25–7.35 (m, 1H), 7.4–7.55 (m, 2H), 7.73 (d, 2H, J=9.0 Hz), 8.83 (d, 1H, J=1.9 Hz), 10.66 (d, 1H, J=1.9 Hz).

TOF-Mass: 447 (M+Na), 463 (M+K).

[α]$_D$ 5.9° (c=0.1, MeOH)

EXAMPLE 5

Preparation of (2R,3R,4R,5R)-3,4,5-trihydroxy-1-(4'-phenoxybenzenesulfonyl)-piperidine-2-carboxylic Acid Hydroxamide:

(1) (2R,4'S,4"R,5'R)-(4-phenoxybenzenesulfonylamino)-(2',2',2",2"-tetramethyl-[4',4"]bis[[1,3]dioxolanyl]-5'-yl)-acetic Acid Methyl Ester

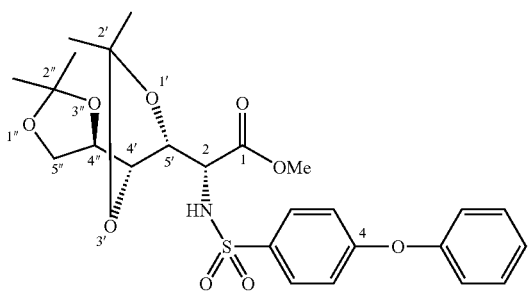

A known compound [(2R,4'S,4"R,5'R)-azide-(2',2',2",2"-tetramethyl-[4',4"]bis[[1,3]dioxolanyl]-5'-yl)-acetic acid methyl ester, 30.1 g] was dissolved in ethyl acetate (300 mL) and 10% Pd—C (4.3 g) was added, and then the mixture was stirred under a hydrogen pressure at 40° C. for 4 hours. The catalyst was removed by filtration and the filtrate was concentrated under reduced pressure. The resulting residue was dissolved in DMF (390 mL) and DMAP (18.1 g) and p-phenoxybenzenesulfonyl chloride (34.5 g) were added, followed by stirring overnight at room temperature. To the reaction solution was added ethyl acetate (700 mL) and, after washing in turn with 1N hydrochloric acid, an aqueous saturated sodium hydrogencarbonate solution, water and saturated saline, the organic layer was dried over magnesium sulfate and the solvent was distilled off under reduced pressure. The resulting residue was purified by silica gel medium pressure column chromatography (ethyl acetate:n-hexane=1:3→2:3) to obtain the titled compound (38.3 g).

$^1$H-NMR(CDCl$_3$) δ: 1.33 (s, 3H), 1.37 (s, 3H), 1.40 (s, 3H), 1.48 (s, 3H), 3.57 (s, 3H), 3.85–4.3 (m, 6H), 5.46 (d, 1H, J=10.5 Hz), 6.95–7.1 (m, 4H), 7.15–7.3 (m, 1H), 7.35–7.5 (m, 2H), 7.7–7.85 (m, 2H).

(2) (1R,2R,4'R,5'S)-[5'-(1",2"-dihydroxy-ethyl)-2',2'-dimethyl-[1,3]dioxolan-4'-yl]-(4-phenoxybenzene-sulfonylamino)-acetic Acid Methyl Ester

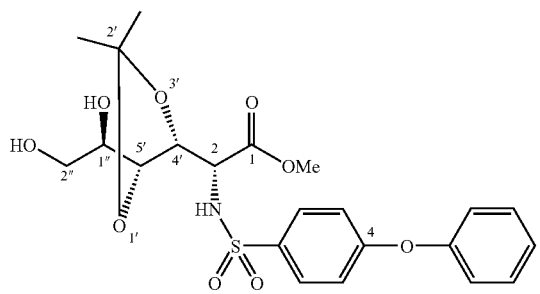

The above compound (1) (25.8 g) was dissolved in acetonitrile (300 mL) and cerium (III) chloride heptahydrate (36.9 g) and oxalic acid (223 mg) were added, and then the mixture was stirred at room temperature for 70 minutes. After neutralizing with sodium carbonate, the insoluble material was removed by filtration and washed with ethyl acetate. The filtrate and the washing were combined and concentrated under reduced pressure, and then the resulting residue was purified by silica gel medium pressure column chromatography (ethyl acetate:n-hexane=2:3→3:1) to obtainthe titled compound (16.0 g), and a starting material (7.0 g) was recovered.

$^1$H-NMR(CDCl$_3$) δ: 1.35 (s, 3H), 1.42 (s, 3H), 2.61 (bs, 1H), 3.61 (s, 3H), 3.65–3.95 (m, 3H), 4.05–4.25 (m, 1H), 4.25–4.4 (m, 2H), 5.46 (d, 1H, J=8.6 Hz), 6.95–7.1 (m, 4H), 7.15–7.3 (m, 1H), 7.3–7.5 (m, 2H), 7.7–7.85 (m, 2H).

(3) (1"S,2R,4'R,5'S)-[5'-(1"-hydroxy-2"-methane-sulfonyloxy-ethyl)-2',2'-dimethyl-[1,3]dioxolan-4'-yl]-(4-phenoxybenzenesulfonylamino)-acetic Acid Methyl Ester

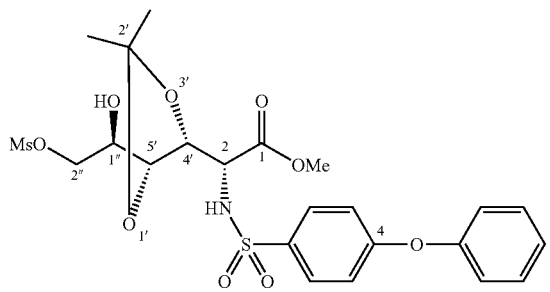

The compound (25.0 g) obtained in accordance with the procedure described in above (2) was dissolved in methylene chloride (430 mL) and triethylamine (5.79 g) was added and, after cooling to −40° C., mesyl chloride (6.25 g)/methylene chloride (20 mL) was slowly added dropwise and the mixture was stirred at the same temperature for one hour. The reaction solution was washed with water and the organic layer was dried over magnesium sulfate, and then the solvent was distilled off under reduced pressure. The resulting residue was purified by silica gel medium pressure column chromatography (ethyl acetate:cyclohexane=35:65→2:3→1:1) to obtain the titled compound (13.5 g).

$^1$H-NMR(CDCl$_3$) δ: 1.34 (s, 3H), 1.41 (s, 3H), 2.91 (d, 1H, J=6.5 Hz), 3.13 (s, 3H), 3.61 (s, 3H), 3.85–4.0 (m, 1H), 4.05–4.28 (m, 2H), 4.28–4.4 (m, 2H), 4.54 (dd, 1H, J=2.5, 11.1 Hz), 5.47 (d, 1H, J=9.5 Hz), 6.95–7.1 (m, 4H), 7.15–7.3 (m, 1H), 7.35–7.5 (m, 2H), 7.7–7.85 (m, 2H).

(4) (3aR,4R,7R,7aR)-7-hydroxy-2,2-dimethyl-5-(4'-phenoxybenzenesulfonyl)-hexahydro-[1,3]dioxolo[4,5-c]pyridine-4-carboxylic Acid Methyl Ester

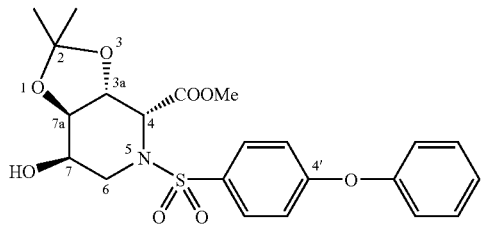

The above compound (3) (13.5 g) was dissolved in DMF (320 mL) and potassium carbonate (4.0 g) was added, and then the mixture was stirred at 45° C. for one hour and 10 minutes. To the reaction solution was added ethyl acetate (500 mL) and, after washing with water and saturated saline (×2), the organic layer was dried over magnesium sulfate and the solvent was distilled off under reduced pressure. The resulting residue was purified by silica gel medium pressure column chromatography (ethyl acetate:cyclohexane=2:3) to obtain the titled compound (10.3 g).

$^1$H-NMR(CDCl$_3$) δ: 1.35 (s, 3H), 1.44 (s, 3H), 2.23 (s, 1H), 3.65 (s, 3H), 3.65–3.75 (m, 1H), 3.82 (dd, 1H, J=2.5, 9.8 Hz), 4.0–4.2 (m, 2H), 4.3–4.4 (m, 1H), 5.05 (d, 1H, J=6.3 Hz), 6.95–7.1 (m, 4H), 7.15–7.25 (m, 1H), 7.35–7.45 (m, 2H), 7.7–7.8 (m, 2H).

(5) (3aR,4R,7R,7aR)-7-hydroxy-2,2-dimethyl-5-(4'-phenoxybenzenesulfonyl)-hexahydro-[1,3]dioxolo[4,5-c]pyridine-4-carboxylic Acid Benzyloxyamide

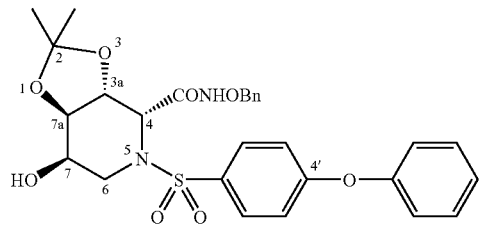

The above compound (4) (10.2 g) was dissolved in a solvent mixture of methanol/1,4-dioxane (30–150 mL) and an aqueous 1N sodium hydroxide solution (55 mL) was added, and then the mixture was stirred at room temperature for one hour and 10 minutes. The reaction solution was neutralized with an aqueous 5% citric acid solution and then extracted with ethyl acetate. The organic layer was washed with water and saturated saline and dried over magnesium sulfate, and then the solvent was distilled off under reduced pressure. The resulting residue was dissolved in DMF (200 mL) and WSC (5.48 g) and HOBt (3.86 g) were added. Subsequently, benzylhydroxylamine hydrochloride (4.56 g) and a DMF (50 mL) solution of DIEA (3.70 g) were added, followed by stirring at room temperature for 2 hours and 30 minutes. To the reaction solution was added ethyl acetate (500 mL) and, after washing in turn with 0.5N hydrochloric acid, an aqueous saturated sodium hydrogencarbonate solution, water and saturated saline, the organic layer was dried over magnesium sulfate and the solvent was distilled off under reduced pressure. The resulting residue was purified by silica gel medium pressure column chromatography (ethyl acetate:cyclohexane=1:1) to obtain the titled compound (8.9 g) as a colorless powder.

$^1$H-NMR(CDCl$_3$) δ: 1.28 (s, 3H), 1.42(s, 3H), 2.39 (s, 1H), 3.39 (d, 1H, J=14.5 Hz), 3.61 (d, 1H, J=9.1 Hz), 4.05–4.25 (m, 1H), 4.28 (s, 1H), 4.83 (d, 1H, J=11.2 Hz), 4.92 (d, 1H, J=11.2 Hz), 5.07 (d, 1H, J=5.4 Hz), 6.95–7.1 (m, 4H), 7.15–7.25 (m, 1H), 7.3–7.5 (m, 7H), 7.8–7.9 (m, 2H), 8.94 (s, 1H).

(6) (2R,3R,4R,5R)-3,4,5-trihydroxy-1-(4'-phenoxybenzenesulfonyl)-piperidine-2-carboxylic Acid Benzyloxyamide:

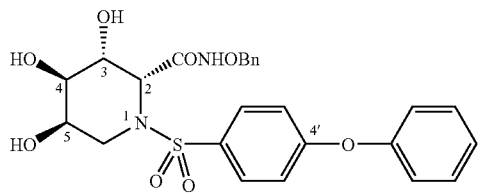

The above compound (5) (8.68 g) was dissolved in methanol (350 mL) and a cation exchange resin (Muromac, 19.0 g) was added, and then the mixture was stirred overnight at room temperature. The insoluble material was removed by filtration and the filtrate was concentrated under reduced pressure. The resulting residue was purified by silica gel medium pressure column chromatography (chloroform:methanol=1:0→30:1→20:1→10:1) to obtain the titled compound (7.35 g) as a colorless powder.

$^1$H-NMR(DMSO-$d_6$) δ: 3.65–3.90 (m, 5H), 4.15 (d, 1H, J=6.1 Hz), 4.52 (d, 1H, J=10.5 Hz), 4.59 (d, 1H, J=10.5 Hz), 4.65–4.75 (m, 2H), 5.26 (d, 1H, J=4.3 Hz), 6.95–7.1 (m, 4H), 7.15–7.25 (m, 1H), 7.3–7.45 (m, 7H), 7.78 (d, 2H, J=8.8 Hz), 11.2 (s, 1H).

(7) (2R,3R,4R,5R)-3,4,5-trihydroxy-1-(4'-phenoxybenzenesulfonyl)-piperidine-2-carboxylic Acid Hydroxamide

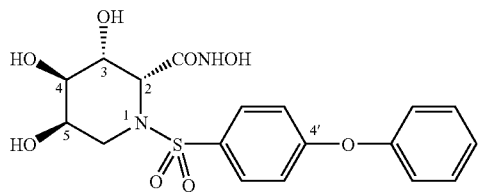

The above compound (6) (6.0 g) was dissolved in methanol (180 mL) and 10% Pd—C (1.3 g) was added, and then the mixture was stirred under a hydrogen atmosphere at 45° C. for 2 hours and 30 minutes. The catalyst was removed by filtration and the filtrate was concentrated under reduced pressure. The resulting residue was purified by silica gel medium pressure column chromatography (chloroform:methanol=20:1→10:1→5:1) to obtain the titled compound (3.76 g) as a colorless powder.

Melting point: 103.5–112° C.

$^1$H-NMR(DMSO-$d_6$) δ: 3.5–3.95 (m, 5H), 4.13 (d, 1H, J=6.5 Hz), 4.55–4.7 (m, 2H), 5.16 (d, 1H, J=4.3 Hz), 7.04 (d, 2H, J=8.8 Hz), 7.14 (d, 2H, J=7.6 Hz), 7.25 (t, 1H, J=7.3 Hz), 7.4–7.55 (m, 2H), 7.78 (d, 2H, J=8.8 Hz), 8.76 (s, 1H), 10.56 (s, 1H).

TOF-Mass: 425(M+H), 447(M+Na), 453 (M+K).

[α]$_D$ 36° (c=0.1, MeOH)

EXAMPLE 6

Preparation of (3aS,4R,7R,7aR)-7-hydroxy-5-(4'-methoxybenzenesulfonyl)-2,2-dimethyl-hexahydro-[1,3]dioxolo[4,5-c]pyridine-4-carboxylic Acid Hydroxyamide

(1) (3S,4'S,5'R)-3-[5'-(tert-butyldimethylsilanyloxymethyl)-2',2'-dimethyl-[1,3]dioxolan-4'-yl]-2-(4''-methoxybenzenesulfonylamino)-3-(tetrahydropyranyloxy)-propionic Acid Benzyl Ester

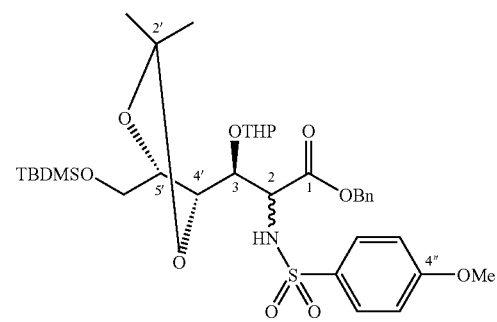

A known compound (IVa) [compound of the general formula (IV) wherein $R^1$ is a methoxy group and an acetoxy group at the 3-position is a hydroxyl group, 21 g] was dissolved in methylene chloride (150 mL) and dihydropyran (5.79 g) and p-toluenesulfonic acid monohydrate (200 mg) were added, and then the mixture was stirred at room temperature for 2.5 hours. To the reaction solution was added chloroform (50 mL) and, after washing with saturated saline, the solution was dried over magnesium sulfate and the solvent was distilled off under reduced pressure. The resulting residue was purified by silica gel medium pressure column chromatography (ethyl acetate:n-hexane=1:7→1:6→1:5→1:4) to obtain the titled compound (16.7 g) as a syrup.

$^1$H-NMR(CDCl$_3$) δ: 0.01–0.06 (m), 0.8–1.0 (m), 1.2–1.8 (m), 3.0–3.25 (m), 3.5–4.2 (m), 4.2–4.65 (m), 4.8–5.15 (m), 5.37 (d, J=10.7 Hz), 5.49 (d, J=8.6 Hz), 5.54 (d, J=9.9 Hz), 6.60 (d, J=10.5 Hz), 6.8–6.95 (m), 7.2–7.4 (m), 7.7–7.85 (m).

(2) (3S,4'S,5'S)-3-[5'-hydroxymethyl-2',2'-dimethyl-[1,3]dioxolan-4'-yl]-2-(4''-methoxybenzenesulfonylamino)-3-(tetrahydropyranyloxy)-propionic Acid Benzyl Ester

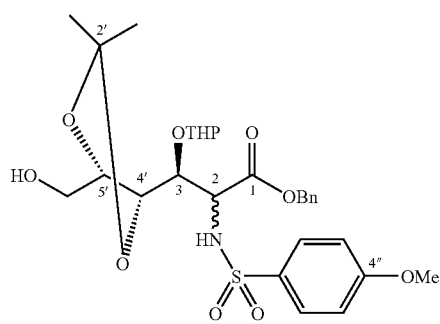

The above compound (1) (16.7 g) was dissolved in THF (200 mL) and acetic acid (3.9 g) and TBAF (64.8 mL) were added, and then the mixture was stirred overnight at room temperature. The reaction solution was concentrated under reduced pressure and ethyl acetate (100 mL) was added and, after washing with water, the solution was dried over magnesium sulfate and the solvent was distilled off under reduced pressure. The resulting residue was purified by silica gel medium pressure column chromatography (ethyl acetate:cyclohexane=1:1→2:1) to obtain the titled compound (12.9 g) as a syrup.

$^1$H-NMR(CDCl$_3$) δ: 1.1–1.6 (m), 3.0–3.3 (m), 3.5–4.0 (m), 4.0–4.25 (m), 4.25–4.65 (m), 4.9–5.2 (m), 5.37 (d, J=10.8 Hz), 5.49 (d, J=8.1 Hz), 5.57 (d, J=9.8 Hz), 6.57 (d, J=10.4 Hz), 6.8–7.0 (m), 7.2–7.4 (m), 7.7–7.85 (m).

(3) (3aS,6R,7S,7aS)-5-(4'-methoxybenzenesulfonyl)-2,2-dimethyl-7-(tetrahydropyranyloxy)-hexahydro-[1,3]dioxolo[4,5-c]pyridine-6-carboxylic Acid Benzyl Ester

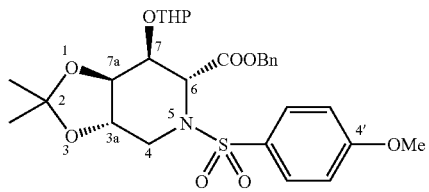

The above compound (2) (12.8 g) was dissolved in THF (200 mL) and triphenylphosphine (13.9 g) and DEAD (8.95 g) were added, and then the mixture was stirred at room temperature for 1.25 hours. To the reaction solution was added ethyl acetate (150 mL) and, after washing with water, the solution was dried over magnesium sulfate and the solvent was distilled off under reduced pressure. The resulting residue was purified by silica gel medium pressure column chromatography (ethyl acetate:cyclohexane=1:3) to obtain the titled compound (10.7 g) as a syrup.

$^1$H-NMR(CDCl$_3$) δ: 1.2–1.5 (m, 6H), 1.5–2.0 (m, 6H), 3.15–3.3 (m, 2H), 3.5–3.7 (m, 1H), 3.75–4.2 (m, 3H), 3.86 (s, 3H), 4.75–4.85 (m, 1H), 4.9–4.95 (m, 1H), 5.0–5.3 (m, 3H), 6.8–6.95 (m, 2H), 7.25–7.5 (m, 5H), 7.7–7.9 (m, 2H).

(4) (2R,3S,4R,5S)-3,4,5-trihydroxy-1-(4'-methoxybenzenesulfonyl)-piperidine-2-carboxylic Acid Benzyl Ester

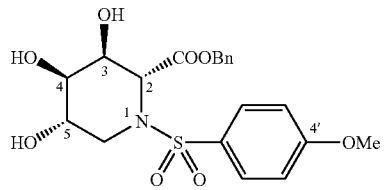

The above compound (3) (10.6 g) was dissolved in methanol (110 mL) and a cation exchange resin (Muromac, 50 g) was added, and then the mixture was stirred overnight at room temperature. The insoluble material was removed by filtration and the filtrate was concentrated under reduced pressure. The resulting residue was purified by silica gel medium pressure column chromatography (chloroform:methanol 50:1→30:1→10:1) to obtain the titled compound (7.4 g) as a syrup.

$^1$H-NMR(CDCl$_3$) δ: 2.95 (t, 1H, J=11.1 Hz), 3.3–3.6 (m, 2H), 3.7–4.0 (m, 4H), 3.82 (s, 3H), 4.53 (bs, 1H), 4.9–5.2 (m, 3H), 6.82 (d, 2H, J=8.9 Hz), 7.2–7.4 (m, 5H), 7.73 (d, 2H, J=8.9 Hz).

(5) (3aS,4R,7S,7aR)-7-hydroxy-5-(4'-methoxybenzenesulfonyl)-2,2-dimethyl-hexahydro-[1,3]dioxolo[4,5-c]pyridine-4-carboxylic Acid Benzyl Ester

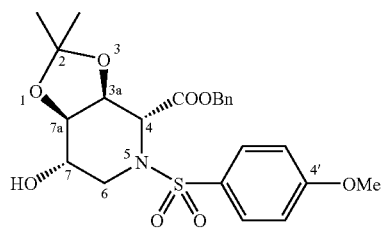

The above compound (4) (7.4 g) was dissolved in DMF (80 mL) and DMP (17.6 g) and p-toluenesulfonic acid monohydrate (70 mg) were added, and then the mixture was stirred overnight at room temperature and further stirred at 60° C. for 1.5 hours. To the reaction solution was added ethyl acetate (150 mL) and, after washing with an aqueous saturated sodium hydrogencarbonate solution and saturated saline (×3), the organic layer was dried over magnesium sulfate and the solvent was distilled off under reduced pressure. The resulting residue was purified by silica gel medium pressure column chromatography (ethyl acetate:cyclohexane=1:3→1:2→1:1) to obtain the titled compound (6.3 g) as a syrup.

$^1$H-NMR(CDCl$_3$) δ: 1.77 (s, 3H), 1.28 (s, 3H), 3.03 (d, 1H, J=6.3 Hz), 3.30 (dd, 1H, J=3.1, 12.1 Hz), 3.3–3.5 (m, 1H), 3.75–3.85 (m, 1H), 3.86 (s, 3H), 4.08 (dd, 1H, J=2.0, 5.7 Hz), 4.73 (dd, 1H, J=1.8, 6.8 Hz), 4.96 (d, 1H, J=1.8 Hz), 5.19 (d, 1H, J=12.2 Hz), 5.26 (d, 1H, J=12.2 Hz), 6.92 (d, 2H, J=9.0 Hz), 7.4 (s, 5H), 7.78 (d, 2H, J=9.0 Hz).

(6) (3aS,4R,7R,7aR)-7-acetoxy-5-(4'-methoxybenzenesulfonyl)-2,2-dimethyl-hexahydro-[1,3]dioxolo[4,5-c]pyridine-4-carboxylic Acid Benzyl Ester

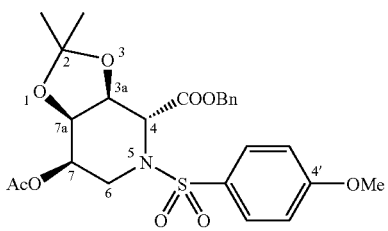

The above compound (5) (4.1 g) was dissolved in methylene chloride/pyridine (60–10 mL) and trifluoromethanesulfonic anhydride (2.89 mL) was adding under stirring at −20° C., and then the mixture was stirred at the same temperature for 30 minutes. To the reaction solution was added chloroform (50 mL) and, after washing with 1N hydrochloric acid and saline, the solution was dried over magnesium sulfate and the solvent was distilled off under reduced pressure. The resulting residue was purified by silica gel column chromatography (ethyl acetate:n-hexane 1:1) to obtain a compound, which was dissolved in acetonitrile (60 mL) and cesium acetate (1.77 g) and 18-Crown-6 (3.05 g) were added, followed by stirring at room temperature for 2 hours. To the reaction solution was added ethyl acetate (100 mL) and, after washing with saturated saline, the solution was dried over magnesium sulfate and the solvent was distilled off under reduced pressure. The resulting residue was purified by silica gel column chromatography (ethyl acetate:cyclohexane=1:4→1:3) to obtain the titled compound (791 mg) as a syrup.

$^1$H-NMR(CDCl$_3$) δ: 1.18 (s, 3H), 1.33 (s, 3H), 1.93 (s, 3H), 3.26 (dd, 1H, J=5.9, 12.5 Hz), 3.67 (dd, 1H, J=4.3, 13.0 Hz), 3.87 (s, 3H), 4.15–4.25 (m, 1H), 4.8–4.9 (m, 2H), 5.14 (d, 1H, J=1.8 Hz), 5.23 (d, 1H, J=12.4 Hz), 5.28 (d, 1H, J=12.4 Hz), 6.93 (d, 2H, J=9.0 Hz), 7.3–7.5 (m, 5H), 7.84 (d, 2H, J=9.0 Hz).

(7) (3aS,4R,7R,7aR)-7-hydroxy-5-(4'-methoxybenzenesulfonyl)-2,2-dimethyl-hexahydro-[1,3]dioxolo[4,5-c]pyridine-4-carboxylic Acid Benzyloxyamide

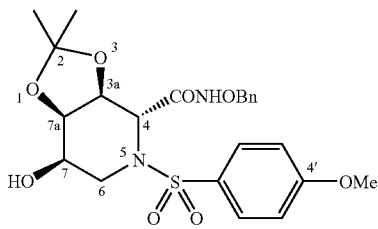

The above compound (6) (730 mg) was dissolved in methanol (10 mL) and 28% NaOMe (132 mg) was added, and then the mixture was stirred at room temperature for one hour. Furthermore, 28% NaOMe (132 mg) was added and, after stirring at room temperature for one hour, the reaction solution was mixed with ethyl acetate (100 mL) and then washed with 1N hydrochloric acid and saturated saline. The organic layer was dried over magnesium sulfate and the solvent was distilled off under reduced pressure, and then the resulting residue was purified by silica gel medium pressure column chromatography (ethyl acetate:n-hexane=1:1) to obtain the titled compound (587 mg) as an amorphous.

$^1$H-NMR(CDCl$_3$) δ: 0.93 (s, 3H), 1.23 (s, 3H), 3.10 (dd, 1H, J=2.4, 11.8 Hz), 3.29 (d, 1H, J=6.6 Hz), 3.45–3.55 (m, 1H), 3.7–3.8 (m, 1H), 3.90 (s, 3H), 4.1–4.2 (m, 1H), 4.6 (d, 1H, J=2 Hz), 4.74 (dd, 1H, J=2.0, 7.3 Hz), 4.99 (s, 2H), 7.01 (d, 2H, J=9 Hz), 7.35–7.55 (m, 5H), 7.77 (d, 2H, J=9 Hz), 9.36 (s, 1H).

(8) (3aS,4R,7R,7aR)-7-hydroxy-5-(4'-methoxybenzenesulfonyl)-2,2-dimethyl-hexahydro-[1,3]dioxolo[4,5-c]pyridine-4-carboxylic Acid Hydroxyamide

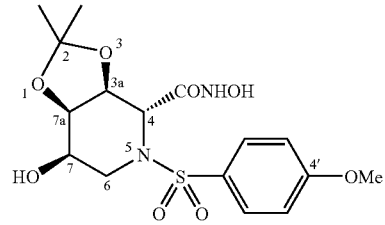

The above compound (7) (278 mg) was dissolved in ethyl acetate (15 mL) and 10% Pd—C (38 mg) was added, and then the mixture was stirred under a hydrogen atmosphere room temperature for 2 hours. The catalyst was removed by filtration and the filtrate was concentrated under reduced pressure. The resulting residue was purified by silica gel medium pressure column chromatography (chloroform:methanol=50:1→30:1→10:1) and then freeze-dried to obtain the titled compound (205 mg) as a colorless amorphous.

$^1$H-NMR(DMSO-d$_6$) δ: 0.99 (s, 3H), 1.18 (s, 3H), 3.20 (dd, 1H, J=2.1, 10.8 Hz), 3.25–3.45 (m, 2H), 3.80 (s, 3H), 3.92 (t, 1H, J=5.3 Hz), 4.28 (d, 1H, J=6.2 Hz), 4.53 (s, 1H), 5.92 (d, 1H, J=6.6 Hz), 7.14 (d, 2H, J=9.0 Hz), 7.75 (d, 2H, J=9.0 Hz), 9.28 (s, 1H), 11.12 (s, 1H).

TOF-Mass: 425 (M+Na), 441 (M+K).

EXAMPLE 7

Preparation of (3aR,4R,7R,7aR)-7-hydroxy-5-(4'-methoxybenzenesulfonyl)-2,2-dimethyl-hexahydro-[1,3]dioxolo[4,5-c]pyridine-4-carboxylic Acid Benzyloxyamide (1) (3aR,4R,7S,7aR)-7-hydroxy-5-(4'-methoxybenzenesulfonyl)-2,2-dimethyl-hexahydro-[1,3]dioxolo[4,5-c]pyridine-4-carboxylic Acid Benzyloxyamide

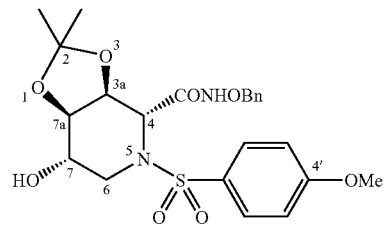

The compound (1.5 g) of Example 2 (4) was dissolved in methanol (30 mL) and an aqueous 1N sodium hydroxide solution (9.5 mL) was added, and then the mixture was stirred at room temperature for one hour. Furthermore, an aqueous sodium hydroxide (4 mL) and 1,4-dioxane (4 mL) were added, followed by stirring for one hour. To the reaction solution was added water (50 mL) and, after washing with ether, the aqueous layer was acidified with an aqueous 10% citric acid solution and extracted with ethyl acetate. The organic layer was washed with water and saturated saline and dried over magnesium sulfate, and then the solvent was distilled off under reduced pressure. The resulting residue was dissolved in DMF (35 mL) and WSC (932 mg) and HOBt (744 mg) were added. Subsequently, benzylhydroxylamine hydrochloride (776 mg) and DIEA (628 mg) were added, followed by stirring overnight at room temperature. To the reaction solution was added ethyl acetate (150 mL) and, after washing in turn with an aqueous 10% citric acid solution, an aqueous saturated sodium hydrogencarbonate solution, water and saturated saline, the organic layer was dried over magnesium sulfate and the solvent was distilled off under reduced pressure. The resulting residue was purified by silica gel medium pressure column chromatography (ethyl acetate:cyclohexane=2:3→1:1) to obtain the titled compound (910 mg).

$^1$H-NMR(CDCl$_3$) δ: 1.23 (s, 3H), 1.42 (s, 3H), 2.35 (d, 1H, J=4.6 Hz), 2.9 (dd, 1H, J=9.8, 12.1 Hz), 3.4–3.55 (m, 1H), 3.59 (dd, 1H, J=5.6, 9.6 Hz), 3.75–4.0 (m, 2H), 3.87 (s, 3H), 4.1 (d, 1H, J=14.3 Hz), 4.14 (d, 1H, J=14.3 Hz), 5.04 (d, 1H, J=5.2 Hz), 6.98 (d, 2H, J=9.0 Hz), 7.38 (s, 5H), 7.85 (d, 2H, J=9.0 Hz), 8.97 (s, 1H).

(2) (3aR,4R,7R,7aR)-7-acetoxy-5-(4'-methoxybenzenesulfonyl)-2,2-dimethyl-hexahydro-[1,3]dioxolo[4,5-c]pyridine-4-carboxylic Acid Benzyloxyamide

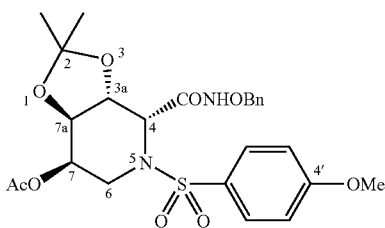

(2-1) (3aR,4R,7S,7aR)-trifluoromethanesulfonic Acid 4-benzyloxycarbamoyl-5-(4'-methoxybenzenesulfonyl)-2,2-dimethyl-hexahydro-[1,3]dioxolo[4,5-c]pyridin-7-yl Ester The above compound (1) (1.0 g) was dissolved in pyridine (10 mL) and trifluoromethanesulfonic anhydride (0.4 mL) was added under stirring at −20° C., and then the mixture was stirred at the same temperature for 2 hours. To the reaction solution was added ethyl acetate (50 mL) and, after washing in turn with dilute hydrochloric acid, an aqueous saturated sodium hydrogencarbonate solution and saline, the solution was dried over magnesium sulfate and the solvent was distilled off under reduced pressure. The resulting residue was purified by silica gel column chromatography (ethyl acetate:n-hexane=1:3→1:2) to obtain the titled compound (670 mg).

$^1$H-NMR(DMSO-d$_6$) δ: 1.18 (s, 3H), 1.41 (s, 3H), 3.82 (s, 3H), 3.75–3.85 (m, 2H), 4.23 (d, 1H, J=5.4, 12 Hz), 4.33 (t, 1H, J=9 Hz), 4.56 (d, 1H, J=12 Hz), 4.62 (d, 1H, J=6 Hz), 4.67 (d, 1H, J=12 Hz), 5.3–5.35 (m, 1H), 7.1–7.2 (m, 2H), 7.3–7.5 (m, 5H), 7.75–7.8 (m, 2H), 11.67 (s, 1H).

(2-2) (3aR,4R,7R,7aR)-7-acetoxy-5-(4'-methoxy-benzenesulfonyl)-2,2-dimethyl-hexahydro-[1,3]dioxolo[4,5-c]pyridine-4-carboxylic Acid Benzyloxyamide The above compound (2-1) (670 mg) was dissolved in acetonitrile (30 mL) and cesium acetate (0.5 g) and 18-Crown-6 (1.4 g) were added, and then the mixture was stirred at room temperature for 16 hours, To the reaction solution was added ethyl acetate (100 mL) and, after washing in turn with dilute hydrochloric acid, an aqueous saturated sodium hydrogencarbonate solution and saturated saline, the solution was dried over magnesium sulfate and the solvent was distilled off under reduced pressure. The resulting residue was purified by silica gel column chromatography (ethyl acetate:n-hexane=1:3→1:1) to obtain the titled compound (161 mg).

$^1$H-NMR(DMSO-d$_6$) δ: 1.26 (s, 3H), 1.33 (s, 3H), 3.82 (s, 3H), 3.75–3.95 (m, 3H), 4.24 (dd, 1H, J=3, 10.2 Hz), 4.63 (d, 1H, J=10.8 Hz), 4.72 (d, 1H, J=10.8 Hz), 4.75 (d, 1H, J=6.6 Hz), 5.35–5.4 (m, 1H), 7.1–7.2 (m, 2H), 7.3–7.45 (m, 5H), 7.7–7.75 (m, 2H), 11.55 (s, 1H).

(3) (3aR,4R,7R,7aR)-7-hydroxy-5-(4'-methoxybenzenesulfonyl)-2,2-dimethyl-hexahydro-[1,3]dioxolo[4,5-c]pyridine-4-carboxylic Acid Benzyloxyamide

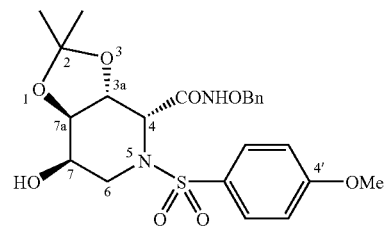

The above compound (2-2) (100 mg) was dissolved in methanol (2 mL) and 28% sodium methoxide (18 mg) was added, and then the mixture was stirred at room temperature for 2 hours. After neutralizing with a cation exchange resin, the insoluble material was removed by filtration and the filtrate was concentrated under reduced pressure. The resulting residue was purified by silica gel column chromatography (ethyl acetate:n-hexane=1:2→1:1→2:1) to obtain the titled compound (69 mg).

$^1$H-NMR(CDCl$_3$) δ: 1.43 (s, 3H), 1.53 (s, 3H), 3.36 (d, 1H, J=14.4 Hz), 3.5–3.65 (m, 1H), 3.86 (s, 3H), 3.8–3.9 (m, 2H), 4.1–4.2 (m, 1H), 4.27 (bs, 1H), 4.86 (d, 1H, J=11.4 Hz), 4.93 (d, 1H, J=11.4 Hz), 5.08 (bs, 1H), 6.9–7.0 (m, 2H), 7.3–7.4 (m, 5H), 7.8–7.9 (m, 2H), 8.88 (s, 1H).

EXAMPLE 8

Preparation of (3aS,4R,7S,7aS)-7-hydroxy-5-(4'-methoxybenzenesulfonyl)-2,2-dimethyl-hexahydro-[1,3]dioxolo[4,5-c]pyridine-4-carboxylic Acid Methyl Ester (1) (2R,4'R,4"S,5'S)-(4-methoxybenzenesulfonylamino)-(2',2',2",2"-tetramethyl-[4',4"]bis[[1,3]dioxolanyl]-5'-yl)-acetic Acid Methyl Ester

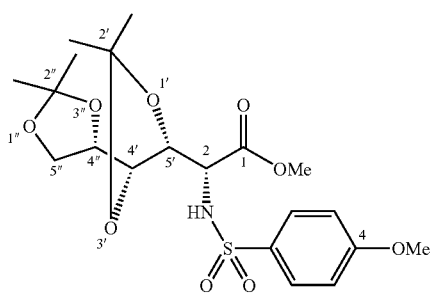

Using a known compound [(2R,4'S,4"R,5'S)-azide-(2',2', 2",2"-tetramethyl-[41,4"]bis[[1,3]dioxolanyl]-5'-yl)-acetic acid methyl ester, 11.7 g], the titled compound (11.9 g) was obtained as a colorless solid in the same manner as in Example 2 (1).

$^1$H-NMR(CDCl$_3$) δ: 1.28 (s, 3H), 1.33 (s, 3H), 1.36 (s, 3H), 1.46 (s, 3H), 3.55 (s, 3H), 3.87 (s, 3H), 3.8–4.0 (m, 3H), 4.05–4.25 (m, 3H), 5.58 (d, 1H, J=7.9 Hz), 6.95 (d, 2H, J=8.9 Hz), 7.78 (d, 2H, J=8.9 Hz).

(2) (1"S,2R,4'S,5'R)-[5'-(1",2"-dihydroxy-ethyl)-2', 2'-dimethyl-[1,3]dioxolan-4'-yl]-(4-methoxybenzenesulfonylamino)-acetic Acid Methyl Ester

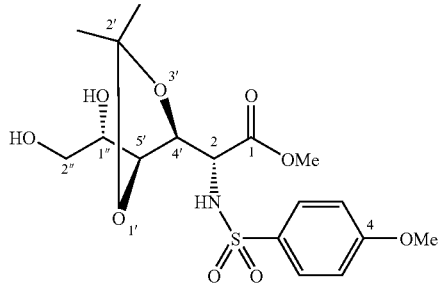

Using the above compound (1) (14.7 g), the titled compound (7.1 g) was obtained in the same manner as in Example 2 (2), and a starting material (4.3 g) was recovered.

$^1$H-NMR(CDCl$_3$) δ: 1.32 (s, 3H), 1.36 (s, 3H), 1.9 (bs, 1H), 3.54 (s, 3H), 3.65–3.8 (m, 2H), 3.86 (s, 3H), 3.8–4.05 (m, 1H), 4.12 (d, 1H, J=5.8 Hz), 4.25–4.34 (m, 1H), 6.97 (d, 2H, J=9.0 Hz), 7.79 (d, 2H, J=9.0 Hz).

(3) (1"R,2R,4'S,5'R)-[5'-(1"-hydroxy-2"-methanesulfonyloxy-ethyl)-2',2'-dimethyl-[1,3]dioxolan-4'-yl]-(4-methoxybenzenesulfonylamino)-acetic Acid Methyl Ester

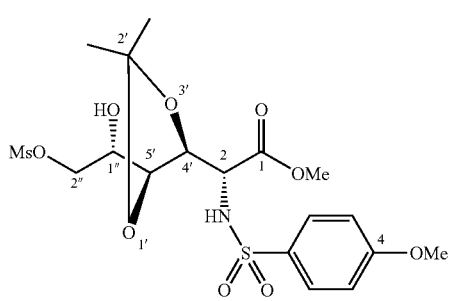

Using the above compound (2) (7.06 g), the titled compound (2.6 g) was obtained in the same manner as in Example 2 (3).

$^1$H-NMR(CDCl$_3$) δ: 1.30 (s, 3H), 1.35 (s, 3H), 3.12 (s, 3H), 3.57 (s, 3H), 3.87 (s, 3H), 3.9–4.0 (m, 2H), 4.0–4.2 (m, 1H), 4.2–4.35 (m, 2H), 4.45–4.55 (m, 1H), 6.98 (d, 2H, J=9.0 Hz), 7.78 (d, 2H, J=9.0 Hz).

(4) (3aS,4R,7S,7aS)-7-hydroxy-5-(4'-methoxybenzenesulfonyl)-2,2-dimethyl-hexahydro-[1,3]dioxolo[4,5-c]pyridine-4-carboxylic Acid Methyl Ester

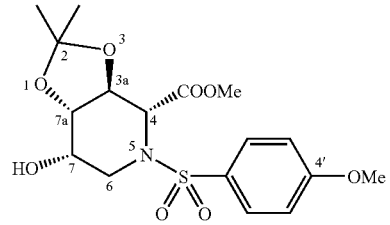

Using the above compound (3) (2.47 g), the titled compound (1.01 g) was obtained as a syrup in the same manner as in Example 2 (4).

$^1$H-NMR(CDCl$_3$) δ: 1.44 (s, 3H), 1.46 (s, 3H), 2.375 (d, 1H, J=1.4 Hz), 3.23 (dd, 1H, J=5.1, 14.7 Hz), 3.46 (dd, 1H, J=4.5, 9.8 Hz), 3.75 (s, 3H), 3.8–3.9 (m, 1H), 3.88 (s, 3H), 4.1–4.2 (m, 1H), 4.35–4.4 (m, 1H), 4.41 (d, 1H, J=8.7 Hz), 6.99 (d, 2H, J=9.0 Hz), 7.80 (d, 2H, J=9.0 Hz).

EXAMPLE 9

Preparation of (3aS,4R,7R,7aS)-7-hydroxy-5-(4'-methoxybenzenesulfonyl)-2,2-dimethyl-hexahydro-[1,3]dioxolo[4,5-c]pyridine-4-carboxylic Acid Benzyloxyamide (1) (2S,4'S,4"R,5'R)-acetoxy-(2',2',2",2"-tetramethyl-[4',4"]bis[[1,3]dioxolanyl]-5'-yl)-acetic Acid Methyl Ester

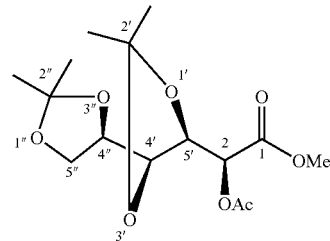

A compound [(2R,4'S,4"R,5'R)-hydroxy-(2',2',2",2"-tetramethyl-[4',4"]bis[[1,3]dioxolanyl]-5'-yl)-acetic acid methyl ester, see Helvetica Chimica Acta, Vol.71, pages 609–618 (1988), 30 g] was dissolved in methylene chloride/pyridine (350–39 mL) and trifluoromethanesulfonic anhydride/methylene chloride (20–10 mL) was added under stirring at −20° C., and then the mixture was stirred at the same temperature for one hour. To the reaction solution was added chloroform (50 mL) and, after washing with water, the solution was dried over magnesium sulfate and the solvent was distilled off under reduced pressure. The resulting residue was purified by silica gel column chromatography (ethyl acetate:n-hexane=1:3) to obtain a compound, which was dissolved in acetonitrile (130 mL) and cesium acetate (4.89 g) and 18-Crown-6 (8.45 g) were added, followed by stirring at room temperature for one hour. To the reaction solution was added ethyl acetate (200 mL) and, after washing with water and saturated saline, the solution was dried over magnesium sulfate and the solvent was distilled off under reduced pressure. The resulting residue was purified by silica gel medium pressure column chromatography (ethyl acetate:n-hexane=1:3) to obtain the titled compound (9.0 g) as a syrup.

$^1$H-NMR(CDCl$_3$) δ: 1.41 (s, 3H), 1.46 (s, 3H), 1.47 (s, 3H), 1.48 (s, 3H), 2.24 (s, 3H), 3.83 (s, 3H), 3.93 (dd, 1H, J=6.7, 8.4 Hz), 4.05–4.2 (m, 2H), 4.5–4.65 (m, 1H), 4.50 (dd, 1H, J=5.3, 7.8 Hz), 5.16 (d, 1H, J=3.1 Hz).

(2) (2S,4'S,4"R,5'R)-hydroxy-(2',2',2",2"-tetramethyl-[4',4"]bis[[1,3]dioxolanyl]-5'-yl)-acetic Acid Methyl Ester

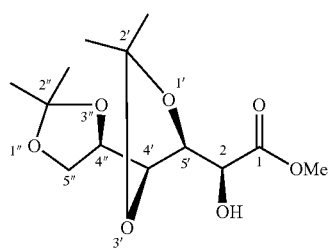

The compound above (1) (9.0 g) was dissolved in methanol (45 mL) and 28% NaOMe (2.61 mL) was added, and then the mixture was stirred at room temperature for 3 hours and 40 minutes. The reaction solution was mixed with ethyl acetate (200 mL) and then washed with 1N hydrochloric acid and saturated saline. The organic layer was dried over magnesium sulfate and the solvent was distilled off under reduced pressure, and then the resulting residue was purified by silica gel medium pressure column chromatography (ethyl acetate:n-hexane=1:3→3:7) to obtain the titled compound (3.0 g) as a syrup.

$^1$H-NMR(CDCl$_3$) δ: 1.41 (s, 3H), 1.42 (s, 3H), 1.43 (s, 3H), 2.0–2.15 (m, 1H), 3.7–4.0 (m, 3H), 3.81 (s, 3H), 4.0–4.15 (m, 1H), 4.38 (dd, 1H, J=5.3, 7.5 Hz).

(3) (2R,4'R,4"R,5'S)-azide-(2',2',2",2"-tetramethyl-[4',4"]bis[[1,3]dioxolanyl]-5'-yl)-acetic Acid Methyl Ester

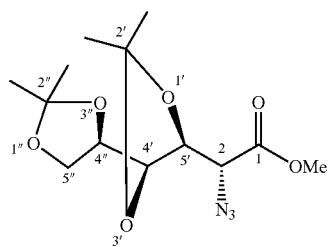

The above compound (2) (3.0 g) was dissolved in methylene chloride/pyridine (50–4 mL) and trifluoromethanesulfonic anhydride (2.0 mL) was added under stirring at −30° C., and then the mixture was stirred at the same temperature for one hour. The reaction solution was mixed with chloroform (50 mL) and then washed with 1N hydrochloric acid and saturated saline. The organic layer was dried over magnesium sulfate and the solvent was distilled off under reduced pressure. Then, the resulting residue was dissolved in DMF (30 mL) and sodium azide (1.21 g) were added, followed by stirring at room temperature for 2.5 hours. To the reaction solution was added ethyl acetate (50 mL) and, after washing with 1N hydrochloric acid and saturated saline, the solution was dried over magnesium sulfate and the solvent was distilled off under reduced pressure. The resulting residue was purified by silica gel medium pressure column chromatography (ethyl acetate:n-hexane=1:3) to obtain the titled compound (2.89 g) as a syrup.

$^1$H-NMR(CDCl$_3$) δ: 1.37 (s, 3H), 1.43 (s, 6H), 1.44 (s, 3H), 3.83 (s, 3H), 3.85–3.95 (m, 1H), 4.0–4.23 (m, 5H), 4.40 (dd, 1H, J=4.8, 7.2 Hz).

(4) (2R,4'R,4"R,5'S)-(4-methoxybenzenesulfonylamino)-(2',2',2',2"-tetramethyl-[4',4"]bis[[1,3]dioxolanyl]-5'-yl)-acetic Acid Methyl Ester

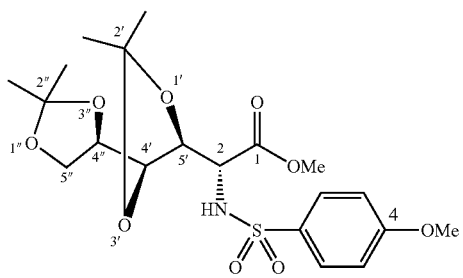

Using the above compound (3) (18.8 g), the titled compound (27.4 g) was obtained as a colorless solid in the same manner as in Example 2 (1).

$^1$H-NMR(CDCl$_3$) δ: 1.32 (s, 3H), 1.378 (s, 3H), 1.382 (s, 3H), 1.44 (s, 3H), 3.50 (s, 3H), 3.87 (s, 3H), 3.85–4.10 (m, 5H), 4.20–4.25 (m, 1H), 5.38 (d, 1H, J=9.5 Hz), 6.97 (d, 2H, J=9.0 Hz), 7.76 (d, 2H, J=9.0 Hz).

(5) (1"R,2R,4'S,5'R)-[5'-(1",2"-dihydroxy-ethyl)-2',2'-dimethyl-[1,3]dioxolan-4'-yl]-(4-methoxybenzenesulfonylamino)-acetic Acid Methyl Ester

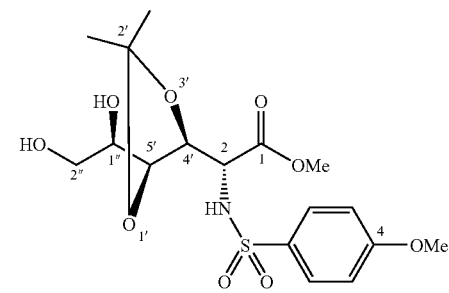

Using the above compound (4) (19.8 g), the titled compound (11.6 g) was obtained in the same manner as in Example 4 (2), and a starting material (2.6 g) was recovered.

$^1$H-NMR(CDCl$_3$) δ: 1.35 (s, 3H), 1.38 (s, 3H), 3.49 (s, 3H), 3.7–3.8 (m, 3H), 3.86 (s, 3H), 3.85–4.25 (m, 3H), 6.97 (d, 2H, J=9.0 Hz), 7.76 (d, 2H, J=9.0 Hz).

(6) (1"S,2R,4'S,5'R)-[5'-(1"-hydroxy-2"-methanesulfonyloxy-ethyl)-2',2'-dimethyl-[1,3]dioxolan-4'-yl]-(4-methoxybenzenesulfonylamino)-acetic Acid Methyl Ester

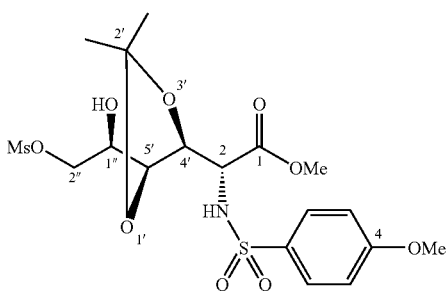

Using the above compound (5) (11.1 g), the titled compound (7.6 g) was obtained in the same manner as in Example 2 (3).

$^1$H-NMR(CDCl$_3$) δ: 1.35 (s, 3H), 1.39 (s, 3H), 2.71 (d, 1H, J=8.0 Hz), 3.13 (s, 3H), 3.51 (s, 3H), 3.87 (s, 3H), 3.9–4.4 (m, 6H), 5.60 (d, 1H, J=9.9 Hz), 6.98 (d, 2H, J=9.0 Hz), 7.77 (d, 2H, J=9.0 Hz).

(7) (3aS,4R,7R,7aS)-7-hydroxy-5-(4'-methoxybenzenesulfonyl)-2,2-dimethyl-hexahydro-[1,3]dioxolo[4,5-c]pyridine-4-carboxylic Acid Methyl Ester

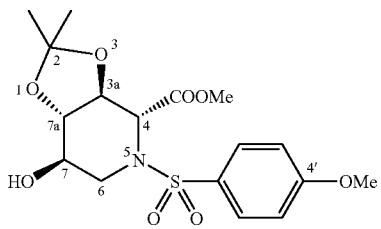

Using the above compound (6) (7.5 g), the titled compound (6.05 g) was obtained as a syrup in the same manner as in Example 2 (4).

$^1$H-NMR(CDCl$_3$) δ: 1.44 (s, 6H), 2.74 (d, 1H, J=7.2 Hz), 3.26 (dd, 1H, J=2.8, 14.9 Hz), 3.45–3.75 (m, 3H), 3.80 (s, 3H), 3.88 (s, 3H), 3.95–4.1 (m, 1H), 4.33 (d, 1H, J=8.9 Hz), 6.99 (d, 2H, J=9.0 Hz), 7.84 (d, 2H, J=9.0 Hz).

(8) (3aS,4R,7R,7aS)-7-hydroxy-5-(4'-methoxybenzenesulfonyl)-2,2-dimethyl-hexahydro-[1,3]dioxolo[4,5-c]pyridine-4-carboxylic Acid Benzyloxyamide

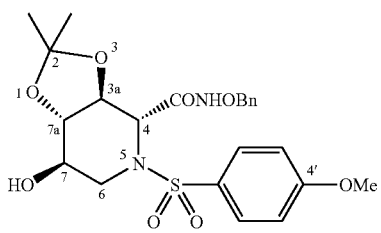

Using the above compound (7) (350 mg), the titled compound (114 mg) was obtained in the same manner as in Example 7 (1).

$^1$H-NMR(CDCl$_3$) δ: 1.35 (s, 3H), 1.41 (s, 3H), 2.57 (d, 1H, J=7.7 Hz), 3.32 (dd, 1H, J=7.3, 10.2 Hz), 3.48 (d, 1H, J=2.8 Hz), 3.87 (s, 3H), 3.85 (dd, 1H, J=8.8, 10.3 Hz), 3.9–4.0 (m, 1H), 4.27 (d, 1H, J=8.5 Hz), 4.93 (d, 1H, J=11.0 Hz), 4.99 (d, 1H, J=10.9 Hz), 6.99 (d, 2H, J=9.0 Hz), 7.3–7.5 (m, 5H), 7.84 (d, 2H, J=9.0 Hz), 8.86 (s, 1H).

EXAMPLE 10

Preparation of Tablets

Tablets each containing 100 mg of (2R,3R,4R,5R)-3,4,5-trihydroxy-1-(4'-phenoxybenzenesulfonyl)-piperidine-2-carboxylic acid hydroxamide (compound e) of Example 5 are obtained by the following procedure.

| [Formulation] | |
|---|---|
| Ingredients | Amount |
| Active principle (Compound e) | 100 Parts by weight |
| Cornstarch | 46 Parts by weight |
| Microcrystalline cellulose | 98 Parts by weight |
| Hydroxypropyl cellulose | 2 Parts by weight |
| Magnesium stearate | 4 Parts by weight |

[Procedure]

An active principle, cornstarch and microcrystalline cellulose are mixed and to the mixture is added hydroxypropyl cellulose dissolved in 50 parts by weight of water, followed by sufficient kneading. The kneaded mixture is passed through a sieve to granulate, dried, mixed with magnesium stearate and then compressed into tablets of 250 mg each.

EXAMPLE 11

Preparation of Granules

Granules containing (2R,3R,4R,5R)-3,4,5-trihydroxy-1-(4'-phenoxybenzenesulfonyl)-piperidine-2-carboxylic acid hydroxamide (compound e) of Example 5 are obtained by the following procedure.

| [Formulation] | |
|---|---|
| Ingredients | Amount |
| Active principle (Compound e) | 200 Parts by weight |
| Lactose | 185 Parts by weight |
| Cornstarch | 109 Parts by weight |
| Hydroxypropyl cellulose | 6 Parts by weight |

[Procedure]

An active principle, lactose and cornstarch are mixed and to the mixture is added hydroxypropyl cellulose dissolved in 120 parts by weight of water, followed by sufficient kneading. The kneaded mixture is passed through a 20 mesh sieve to granulate, dried and then size-adjusted to obtain granules containing 200 mg of an active principle per 500 mg of granule.

EXAMPLE 12

Preparation of Capsules

Capsules each containing 100 mg of (2R,3R,4R,5R)-3,4,5-trihydroxy-1-(4'-phenoxybenzenesulfonyl)-piperidine-2-carboxylic acid hydroxamide (compound e) of Example 5 are obtained by the following procedure.

| [Formulation] | |
|---|---|
| Ingredients | Amount |
| Active principle (Compound e) | 100 Parts by weight |
| Lactose | 35 Parts by weight |
| Cornstarch | 60 Parts by weight |
| Magnesium stearate | 5 Parts by weight |

[Procedure]

The above ingredients are well mixed and 200 mg each of the powder mixture is encapsulated to obtain capsules.

EXAMPLE 13

Preparation of Injections

A mixture of 0.5 parts by weight of (2R,3R,4R,5R)-3,4,5-trihydroxy-1-(4'-phenoxybenzenesulfonyl)-piperidine-2-carboxylic acid hydroxamide (compound e) of Example 5 and 5 parts by weight of sorbitol are dissolved in distilled water for injection to obtain 100 parts by weight of the aqueous solution. The aqueous solution is filtered through a membrane filter. 5 g each of the filtrate is poured into an ample substituted by nitrogen gas. The ample are sealed and then sterilized by heating at 120° C. for 15 minutes to obtain injection containing 25 mg of the compound (e) per ample.

EXAMPLE 14

Preparation of Ointments 1.0 parts by weight of (2R,3R,4R,5R)-3,4,5-trihydroxy-1-(4'-phenoxybenzenesulfonyl)-piperidine-2-carboxylic acid hydroxamide (compound e) and 0.1 parts by weight of butyl paraben are dispersed in 5.0 parts by weight of light liquid paraffin. The mixture is milled in a mortar and sieved through a 200 mesh screen. This product is mixed with 5.0 parts by weight of liquid paraffin and the mixture is mixed with 88.9 parts by weight of gelled hydrocarbon warmed at about 60° C. to take a homogenous dispersion whereupon oily ointment is obtained.

INDUSTRIAL APPLICABILITY

The drugs of the present invention suppress the release of HB-EGF from cell membrane stimulated with 12-O-tetradecanoylphorbol-13-acetate (hereinafter referred to as TPA) (see, Test example 1). They also suppress not only epidermal hyperplasia in mice induced by the application of TPA on their back, but re-epithelialization of keratinocytes mouse skin wound model (see, Test Examples 2 and 3). Severe side effects were not noted in these Test Examples using mice. Thus, the medicine according to the present invention is useful as a keratinocyte-proliferation inhibitor.

The invention claimed is:

1. A compound represented by the following formula:

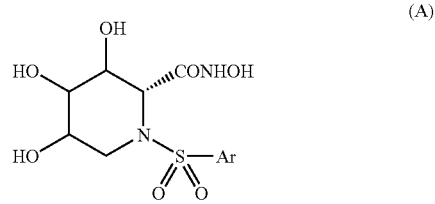

(A)

wherein Ar represents a phenyl group which may have a substituent at the p-position, or a pharmaceutically acceptable salt thereof.

2. A compound represented by the general formula (I):

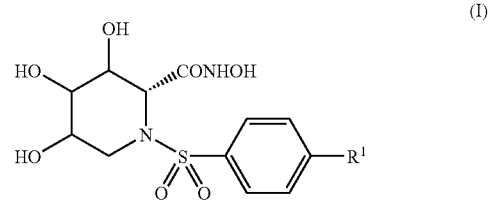

(I)

wherein $R^1$ represents a hydrogen atom, a halogen atom, a hydroxyl group, an amino group, a $C_1$–$C_8$ alkyl group, a phenyl group, a phenoxy group, a $C_1$–$C_8$ alkoxy group (said $C_1$–$C_8$ alkoxy group may be substituted with a $C_1$–$C_4$ alkoxy group or a $C_1$–$C_4$ alkylthio group) or a heteroallyloxy group, or a pharmaceutically acceptable salt thereof.

3. A composition comprising the compound or pharmaceutically acceptable salt thereof according to claim 1 or 2 as an active ingredient.

* * * * *